United States Patent
Petts et al.

(10) Patent No.: US 11,732,205 B2
(45) Date of Patent: *Aug. 22, 2023

(54) COMPOSITIONS AND METHODS AND USES RELATING THERETO

(71) Applicant: Innospec Limited, Ellesmere Port (GB)

(72) Inventors: Matthew Petts, Elton Chester (GB); Katherine Le Manquais, Ellesmere Port (GB); Alan Norman Ross, Wigan (GB)

(73) Assignee: Innospec Limited, Ellesmere Port (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/843,382

(22) Filed: Jun. 17, 2022

(65) Prior Publication Data

US 2022/0403270 A1 Dec. 22, 2022

Related U.S. Application Data

(63) Continuation of application No. 16/494,617, filed as application No. PCT/GB2018/050840 on Mar. 28, 2018, now Pat. No. 11,396,634.

(30) Foreign Application Priority Data

Mar. 30, 2017 (GB) ..................... 1705091

(51) Int. Cl.
  *C10L 1/19* (2006.01)
  *C10L 1/222* (2006.01)
  (Continued)

(52) U.S. Cl.
  CPC ........... *C10L 1/1905* (2013.01); *C10L 1/2222* (2013.01); *C10L 10/04* (2013.01); *C10L 10/08* (2013.01);
  (Continued)

(58) Field of Classification Search
  CPC ...... C10L 1/1905; C10L 1/2222; C10L 10/04; C10L 10/08; C10L 10/18;
  (Continued)

(56) References Cited

U.S. PATENT DOCUMENTS 5,925,151 A 7/1999 DeCanio et al.
10,351,791 B2 7/2019 Reid et al.
(Continued)

FOREIGN PATENT DOCUMENTS

CA 2918061 A1 * 1/2015 ........... C07C 211/63
EP 0565285 A1 10/1993
(Continued)

OTHER PUBLICATIONS

Shanmugam et al., "Design, Synthesis, and Characterization of Bismaleimide Co-Curing Elastomers" I&EC Research 2012.
(Continued)

*Primary Examiner* — Cephia D Toomer
(74) *Attorney, Agent, or Firm* — Burns & Levinson LLP; Rebecca C. Christon

(57) ABSTRACT

A quaternary ammonium compound of formula (I): wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

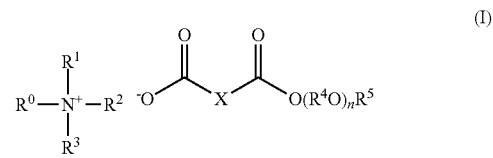

24 Claims, 2 Drawing Sheets

(51) Int. Cl.
*C10L 10/04* (2006.01)
*C10L 10/08* (2006.01)
*C10L 10/18* (2006.01)
*C10M 133/06* (2006.01)
*C10N 30/04* (2006.01)

(52) U.S. Cl.
CPC ........... *C10L 10/18* (2013.01); *C10M 133/06* (2013.01); *C10L 2200/0259* (2013.01); *C10L 2200/0446* (2013.01); *C10L 2230/22* (2013.01); *C10L 2270/02* (2013.01); *C10M 2207/288* (2013.01); *C10M 2215/04* (2013.01); *C10N 2030/04* (2013.01)

(58) Field of Classification Search
CPC ..... C10L 2200/0259; C10L 2200/0446; C10L 2230/22; C10L 2270/02; C10M 133/06; C10M 2207/288; C10M 2215/04; C10N 2030/04
See application file for complete search history.

(56) References Cited

U.S. PATENT DOCUMENTS

| | | |
|---|---|---|
| 2008/0052985 A1 | 3/2008 | Stevenson et al. |
| 2008/0060259 A1 | 3/2008 | Breakspear et al. |
| 2008/0060608 A1 | 3/2008 | Breakspear et al. |
| 2008/0113890 A1 | 5/2008 | Moreton et al. |
| 2008/0307698 A1 | 12/2008 | Barton et al. |
| 2009/0282731 A1 | 11/2009 | Malfer et al. |
| 2011/0258917 A1 | 10/2011 | Garcia Castro et al. |
| 2011/0315107 A1 | 12/2011 | Grabarse et al. |
| 2012/0010112 A1 | 1/2012 | Grabarse et al. |
| 2013/0031827 A1 | 2/2013 | Reid et al. |
| 2017/0121628 A1 | 5/2017 | Moreton et al. |

FOREIGN PATENT DOCUMENTS

| | | |
|---|---|---|
| EP | 1884556 A2 | 2/2008 |
| EP | 1900795 A1 | 3/2008 |
| EP | 2571910 A1 | 3/2013 |
| EP | 2811007 A1 | 6/2013 |
| EP | 2796446 A | 4/2014 |
| GB | 1483199 A | 8/1977 |
| GB | 1548253 A | 7/1979 |
| GB | 2533892 A | 7/2016 |
| RO | 88950 A1 | 4/1986 |
| WO | 2006135881 A1 | 12/2006 |
| WO | 2009040583 A1 | 4/2009 |
| WO | 2010078300 A1 | 7/2010 |
| WO | 2011095819 A1 | 8/2011 |
| WO | 2013017889 A1 | 2/2013 |
| WO | 2015011506 A1 | 1/2015 |
| WO | 2015011507 A1 | 1/2015 |
| WO | 2016016641 A1 | 2/2016 |
| WO | 2017017454 A1 | 2/2017 |

OTHER PUBLICATIONS

International Search Report and Written Opinion issued in PCT/GB2018/050840 dated May 25, 2018.
Combined Search and Examination Report issued in Application No. GB1805073.2 dated Nov. 8, 2018.
Search Report issued in Application No. GB 1705091.5 dated Jan. 17, 2018.

* cited by examiner

COMPOSITIONS AND METHODS AND USES RELATING THERETO

CROSS-REFERENCE TO RELATED APPLICATIONS

This application is a continuation of pending U.S. application Ser. No. 16/494,617 filed on Sep. 16, 2019, which is a U.S. national stage application under 35 U.S.C. 371 of International Application No. PCT/GB2018/050840, filed on Mar. 28, 2018, and entitled COMPOSITIONS AND METHODS AND USES RELATING THERETO, which in turn claims priority to and benefit of Great Britain Patent Application No. 1705091.5, filed Mar. 30, 2017, which is incorporated by reference herein in its entirety for all purposes.

FIELD

The present invention relates to novel quaternary ammonium compounds, to compositions comprising these compounds and methods and uses relating thereto. In particular the invention relates to compositions, methods and uses for improving the performance of engines, especially diesel engines, using fuel additives. In particular the invention relates to additives for diesel fuel compositions for use in diesel engines with high pressure fuel systems.

BACKGROUND

Due to consumer demand and legislation, diesel engines have in recent years become much more energy efficient, show improved performance and have reduced emissions.

These improvements in performance and emissions have been brought about by improvements in the combustion process. To achieve the fuel atomisation necessary for this improved combustion, fuel injection equipment has been developed which uses higher injection pressures and reduced fuel injector nozzle hole diameters. The fuel pressure at the injection nozzle is now commonly in excess of 1500 bar ($1.5 \times 10^8$ Pa). To achieve these pressures the work that must be done on the fuel also increases the temperature of the fuel. These high pressures and temperatures can cause degradation of the fuel. Furthermore, the timing, quantity and control of fuel injection has become increasingly precise. This precise fuel metering must be maintained to achieve optimal performance.

Diesel engines having high pressure fuel systems can include but are not limited to heavy duty diesel engines and smaller passenger car type diesel engines. Heavy duty diesel engines can include very powerful engines such as the MTU series 4000 diesel having 20 cylinder variants designed primarily for ships and power generation with power output up to 4300 kW or engines such as the Renault dXi 7 having 6 cylinders and a power output around 240 kW. A typical passenger car diesel engine is the Peugeot DW10 having 4 cylinders and power output of 100 kW or less depending on the variant.

A common problem with diesel engines is fouling of the injector, particularly the injector body, and the injector nozzle. Fouling may also occur in the fuel filter. Injector nozzle fouling occurs when the nozzle becomes blocked with deposits from the diesel fuel. Fouling of fuel filters may be related to the recirculation of fuel back to the fuel tank. Deposits increase with degradation of the fuel. Deposits may take the form of carbonaceous coke-like residues, lacquers or sticky or gum-like residues. Diesel fuels become more and more unstable the more they are heated, particularly if heated under pressure. Thus diesel engines having high pressure fuel systems may cause increased fuel degradation. In recent years the need to reduce emissions has led to the continual redesign of injection systems to help meet lower targets. This has led to increasingly complex injectors and lower tolerance to deposits.

The problem of injector fouling may occur when using any type of diesel fuels. However, some fuels may be particularly prone to cause fouling or fouling may occur more quickly when these fuels are used. For example, fuels containing biodiesel and those containing metallic species may lead to increased deposits.

When injectors become blocked or partially blocked, the delivery of fuel is less efficient and there is poor mixing of the fuel with the air. Over time this leads to a loss in power of the engine and increased exhaust emissions and poor fuel economy.

Deposits are known to occur in the spray channels of the injector, leading to reduced flow and power loss. As the size of the injector nozzle hole is reduced, the relative impact of deposit build up becomes more significant. Deposits are also known to occur at the injector tip. Here they affect the fuel spray pattern and cause less effective combustion and associated higher emissions and increased fuel consumption.

In addition to these "external" injector deposits in the nozzle hole and at the injector tip which lead to reduced flow and power loss, deposits may occur within the injector body causing further problems. These deposits may be referred to as internal diesel injector deposits (or IDIDs). IDIDs occur further up inside the injector on the critical moving parts. They can hinder the movement of these parts affecting the timing and quantity of fuel injection. Since modern diesel engines operate under very precise conditions these deposits can have a significant impact on performance.

IDIDs cause a number of problems, including power loss and reduced fuel economy due to less than optimal fuel metering and combustion. Initially the engine may experience cold start problems and/or rough engine running. These deposits can lead to more serious injector sticking. This occurs when the deposits stop parts of the injector from moving and thus the injector stops working. When several or all of the injectors stick the engine may fail completely.

IDIDs are recognised as a serious problem by those working in the field and a new engine test has been developed by the industry based organisation, the Coordinating European Council (CEC). The IDID DW10C test was developed to be able to discriminate between a fuel that produces no measurable deposits and one which produces deposits that cause startability issues considered unacceptable. The objective of the test is to discriminate between fuels that differ in their ability to produce IDIDs in direct injection common rail diesel engines.

The present inventors have studied internal diesel injector deposits and have found that they contain a number of components. As well as carbonaceous deposits the presence of lacquers and/or carboxylate residues can lead to injector sticking.

Lacquers are varnish-like deposits which are insoluble in fuel and common organic solvents. Some occurrences of lacquers have been found by analysis to contain amide functionality and it has been suggested that they form due to the presence of low molecular weight amide containing species in the fuel.

Carboxylate residues may be present from a number of sources. By carboxylate residues we mean to refer to salts of carboxylic acids. These may be short chain carboxylic acids but more commonly long chain fatty acid residues are present. The carboxylic residues may be present as ammonium and/or metal salts. Both carboxylic acids and metals may be present in diesel fuel from a number of sources. Carboxylic acids may occur due to oxidation of the fuel, may form during the combustion process and are commonly added into fuel as lubricity additives and/or corrosion inhibitors. Residual fatty acids may be present in the fatty acid methyl esters included as biodiesel and they may also be present as byproducts in other additives. Derivatives of fatty acids may also be present and these may react or decompose to form carboxylic acids.

Various metals may be present in fuel compositions. This may be due to contamination of the fuel during manufacture, storage, transport or use or due to contamination of fuel additives. Metal species may also be added to fuels deliberately. For example, transition metals are sometimes added as fuel borne catalysts to improve the performance of diesel particulate filters.

The present inventors believe that one of the many causes of injector sticking occurs when metal or ammonium species react with carboxylic acid species in the fuel. One example of injector sticking has arisen due to sodium contamination of the fuel. Sodium contamination may occur for a number of reasons. For example, sodium hydroxide may be used in a washing step in the hydrodesulfurisation process and could lead to contamination. Sodium may also be present due to the use of sodium-containing corrosion inhibitors in pipelines. Another example can arise from the presence of calcium from, for example, interaction with or contamination with a lubricant or from calcium chloride used in salt drying processes in refineries. Other metal contamination may occur for example during transportation due to water bottoms.

Metal contamination of diesel fuel and the resultant formation of carboxylate salts is believed to be a significant cause of injector sticking. The formation of lacquers is yet another major cause of injector sticking.

One approach to combatting IDIDs and injector sticking resulting from carboxylate salts is to try to eliminate the source of metal contamination and/or carboxylic acids or to try to ensure that particularly problematic carboxylic acids are eliminated. This has not been entirely successful and there is a need for additives to provide control of IDIDs.

Deposit control additives are often included in fuel to combat deposits in the injector nozzle or at the injector tip. These may be referred to herein as "external injector deposits". Additives are also used to control deposits on vehicle fuel filters. However additives which have been found to be useful to control "external deposits" and fuel filter deposits are not always effective at controlling IDIDs. A challenge for the additive formulator is to provide more effective detergents.

SUMMARY

It is an aim of the present invention to provide methods and uses which improve the performance of a diesel engine, especially a diesel engine having a high pressure fuel system.

This may be achieved for example by preventing or reducing the formation of IDIDs and/or by reducing or removing existing IDIDs. The invention provides methods and uses which control "external injector deposits" and/or fuel filter deposits.

Reducing or preventing the formation of deposits may be regarded as providing "keep clean" performance. Reducing or removing existing deposits may be regarded as providing "clean up" performance. It is an aim of the present invention to provide "keep clean" and/or "clean up" performance.

Many different types of compounds are known in the art for use as detergent additives in fuel oil compositions, for the control of deposits in engines.

The present invention relates to novel quaternary ammonium compounds having an ester counterion that is the partial ester of a polycarboxylic acid that are useful as detergents.

DETAILED DESCRIPTION

Figure 1:
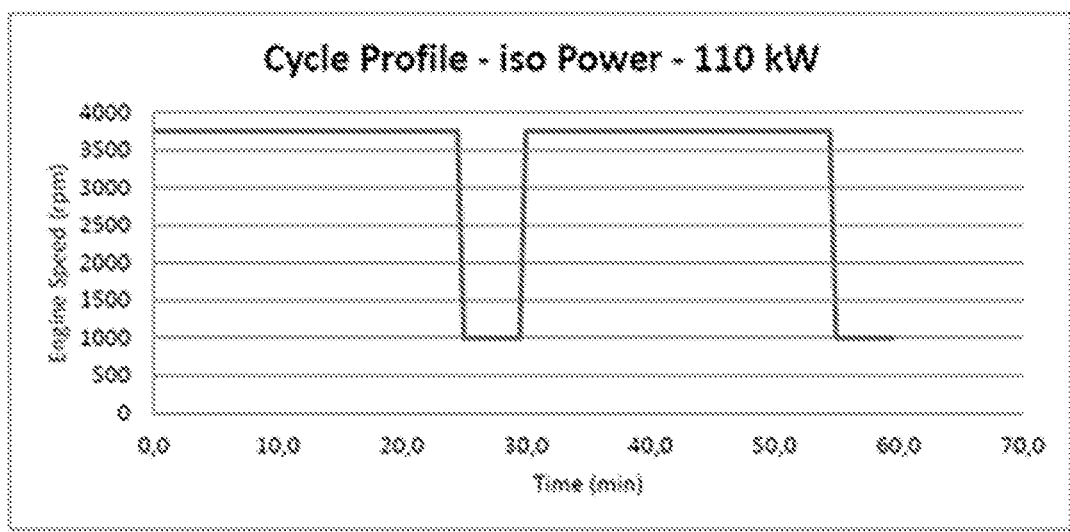
FIG. 1 is a graph of a test procedure consisting of main run cycles followed by soak periods.

According to a first aspect of the present invention there is provided a quaternary ammonium compound of formula (I):

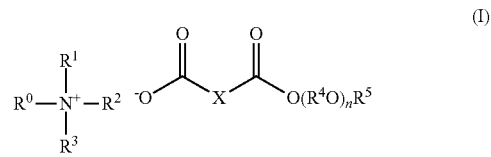

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferably each of $R^0$, $R^1$, $R^2$ and $R^3$ is an optionally substituted alkyl, alkenyl or aryl group.

As used herein, the term "hydrocarbyl" substituent or group is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic (including aliphatic- and alicyclic-substituted aromatic) substituents, as well as cyclic substituents wherein the ring is completed through another portion of the molecule (e.g., two substituents together form a ring);

(ii) substituted hydrocarbon groups, that is, substituents containing non-hydrocarbon groups (e.g., halo (especially chloro and fluoro), hydroxy, alkoxy, keto, acyl, cyano, mercapto, alkylmercapto, amino, alkylamino, nitro, nitroso, and sulphoxy);

(iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

In this specification, unless otherwise stated references to optionally substituted alkyl groups may include aryl-substituted alkyl groups and references to optionally-substituted aryl groups may include alkyl-substituted or alkenyl-substituted aryl groups.

The quaternary ammonium salt of the present invention may be prepared by any suitable means. Suitable methods will be known to the person skilled in the art.

In some embodiments, $R^0$ may be a lower alkyl group and the quaternary ammonium compound is prepared from an ester of formula $R^0OOCXCOO(R^4O)_nR^5$. In such embodiments $R^0$ is preferably methyl.

In some embodiments the quaternary ammonium salt may be prepared from an ester quaternising agent of formula $RCOOR^0$ followed by an ion exchange reaction with an acid of formula $HOOCXCOO(R^4O)_nR^5$. In such embodiments R may be an optionally substituted aryl or alkyl group or an ester. For example $R^0$ may be methyl and $RCOOR^0$ may be methyl salicylate or dimethyl oxalate.

In some embodiments $R^0$ is a C1 to C5 alkyl group, preferably methyl.

In preferred embodiments the quaternary ammonium compound is prepared from a tertiary amine, an acid-activated alkylating agent and an acid. Thus $R^0$ is preferably the residue of an alkylating agent.

In preferred embodiments the first aspect of the present invention provides a quaternary ammonium compound which is the reaction product of:
(a) a tertiary amine of formula $R^1R^2R^3N$;
(b) an acid-activated alkylating agent; and
(c) a compound of formula $HOOCXCOO—(R^4O)_n—R^5$ wherein $R^4$ is an optionally substituted alkylene group, $R^5$ is hydrogen or an optionally substituted alkyl, alkenyl or aryl group and n is 0 or a positive integer, provided that n is not 0 when $R^5$ is hydrogen.

According to a second aspect of the present invention there is provided a method of preparing a quaternary ammonium salt, the method comprising reacting (a) a tertiary amine of formula $R^1R^2R^3N$ with (b) an acid-derived alkylating agent in the presence of (c) a compound of formula $HOOCXCOO—(R^4O)_n—R^5$, wherein $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferred features of the first and second aspects of the invention will now be described.

In this specification any feature of any aspect of the invention may be combined with any feature of any other aspect as appropriate.

X is a linking group. Preferably X is an optionally substituted alkylene or arylene group. X is further defined herein.

The present invention relates to a composition, a method and a use involving a quaternary ammonium salt. This compound may be referred to herein as "the quaternary ammonium salt" or as "the quaternary ammonium compound".

The quaternary ammonium salt may comprise a single compound. In some embodiments mixtures containing more than one quaternary ammonium salt additive may be used. References herein to "a quaternary ammonium salt" of the invention or "the quaternary ammonium salt" include mixtures comprising two or more such compounds.

Component (a) used to prepare the quaternary ammonium salts of the present invention is a tertiary amine. Any suitable tertiary amine may be used.

In some embodiments of the present invention the tertiary amine may be a small compound of low complexity and low molecular weight. In some embodiments the tertiary amine may be a complex molecule and/or a molecule of high molecular weight which includes a tertiary amine moiety.

The tertiary amine compounds of the present invention preferably do not include any primary or secondary amine groups. In some embodiments they may be derived from compounds including these groups but preferably these have been subsequently reacted to form additional tertiary amine species. The tertiary amine compound used as component (a) may contain more than one tertiary amine group. However tertiary amine compounds including primary or secondary amine groups are within the scope of the invention provided these groups do not prevent quaternisation of the tertiary amine species.

Tertiary amines for use herein are preferably compounds of formula $R^1R^2R^3N$, wherein each of $R^1$, $R^2$ and $R^3$ is independently an optionally substituted alkyl, alkenyl or aryl group.

$R^1$, $R^2$ and $R^3$ may be the same or different. In some preferred embodiments $R^1$ and $R^2$ are the same and $R^3$ is different.

Preferably each of $R^1$ and $R^2$ is independently an optionally substituted alkyl, alkenyl or aryl group having from 1 to 50 carbon atoms, preferably from 1 to 40 carbon atoms, more preferably from 1 to 30 carbon atoms.

Each of $R^1$ and $R^2$ may be optionally substituted with one or more groups selected from halo (especially chloro and fluoro), hydroxy, alkoxy, keto, acyl, cyano, mercapto, alkylmercapto, dialkylamino, nitro, nitroso, and sulphoxy. The alkyl groups of these substituents may be further substituted.

Preferably each of $R^1$ and $R^2$ is independently an optionally substituted alkyl or alkenyl group. Preferably each of $R^1$ and $R^2$ is independently an optionally substituted alkyl group. Preferably each of $R^1$ and $R^2$ is independently an optionally substituted alkyl or alkenyl group having from 1 to 50 carbon atoms, preferably from 1 to 40 carbon atoms, more preferably from 1 to 30 carbon atoms, suitably from 1 to 20 carbon atoms, preferably from 1 to 12 carbon atoms, more preferably from 1 to 10 carbon atoms, suitably from 1 to 8 carbon atoms, for example from 1 to 6 carbon atoms.

In some embodiments each of $R^1$ and $R^2$ is methyl and $R^3$ is a $C_6$ to $C_{36}$, preferably a $C_{10}$ to $C_{30}$, alkyl or alkenyl group.

In some embodiments $R^1$ is methyl and each of $R^2$ and $R^3$ is a $C_6$ and $C_{36}$, preferably a $C_{10}$ to $C_{30}$ alkyl or alkenyl group.

Preferably $R^1$ is an optionally substituted alkyl or alkenyl group, preferably having from 1 to 10, preferably from 1 to 4 carbon atoms. Preferably $R^1$ is an alkyl group. It may be a substituted alkyl group, for example a hydroxy substituted alkyl group. Preferably $R^1$ is an unsubstituted alkyl group. The alkyl chain may be straight-chained or branched. In some preferred embodiments $R^1$ is selected from methyl, ethyl, propyl and butyl, including isomers thereof. In some especially preferred embodiments $R^1$ is methyl or ethyl.

Preferably $R^2$ is an optionally substituted alkyl or alkenyl group, preferably having from 1 to 10, preferably from 1 to 4 carbon atoms. Preferably $R^2$ is an alkyl group. It may be a substituted alkyl group, for example a hydroxy substituted alkyl group. Preferably $R^2$ is an unsubstituted alkyl group. The alkyl chain may be straight-chained or branched. In some preferred embodiments $R^2$ is selected from methyl, ethyl, propyl and butyl, including isomers thereof. In some especially preferred embodiments $R^2$ is methyl or ethyl.

In some embodiments $R^3$ is an optionally substituted alkyl or alkenyl group having from 1 to 50 carbon atoms, preferably from 1 to 40 carbon atoms, more preferably from 1 to 30 carbon atoms, suitably from 1 to 20 carbon atoms, preferably from 1 to 12 carbon atoms, more preferably from 1 to 10 carbon atoms, suitably from 1 to 8 carbon atoms, for example from 1 to 6 carbon atoms. Suitable substituents include halo (especially chloro and fluoro), hydroxy, alkoxy, keto, acyl, cyano, mercapto, alkylmercapto, amino, alkylamino, nitro, nitroso, sulphoxy, amido, alkyamido, imido and alkylimido. The alkyl groups of these substituents may be further substituted.

In some embodiments $R^3$ is an optionally substituted alkyl or alkenyl group, preferably having from 1 to 10, preferably from 1 to 4 carbon atoms. Suitably $R^3$ is an optionally substituted alkyl group. In some embodiments $R^3$ is an unsubstituted alkyl group, for example a $C_1$ to $C_{10}$, suitably a $C_1$ to $C_6$ or a $C_1$ to $C_4$ alkyl group. The alkyl group may be straight chain or branched.

In some preferred embodiments $R^3$ is a substituted alkyl group. Preferred substituents include alkoxy and hydroxy groups.

In some embodiments the alkyl chain may be interrupted by one or more heteroatoms, for example one or more oxygen atoms.

In some preferred embodiments $R^3$ is a hydroxy-substituted alkyl group. The alkyl chain may be straight-chained or branched. In some especially preferred embodiments $R^3$ is a hydroxyethyl group.

In one embodiment $R^3$ is a hydroxyethyloxyethyl group.

In some embodiments each of $R^1$, $R^2$ and $R^3$ is independently selected from an alkyl or hydroxyalkyl group having 1 to 12, preferably 1 to 6, more preferably 1 to 4 carbon atoms.

In some embodiments trialkylamines and hydroxyalkyl diakyl amines are especially preferred.

In some embodiments $R^3$ is an optionally substituted hydrocarbyl group, for example an optionally substituted hydrocarbyl group having from 1 to 300 carbon atoms, for example from 1 to 200 carbon atoms. $R^3$ may be an optionally substituted hydrocarbyl group having a number average molecular weight of from 100 to 5000, preferably from 500 to 2500.

In some embodiments $R^3$ is an optionally substituted aryl group or alkaryl group. For example $R^3$ may be benzyl.

In some embodiments $R^3$ is an optionally substituted alkyl or alkenyl group. $R^3$ may be an unsubstituted alkyl or alkenyl group. Suitably $R^3$ is an alkyl or alkenyl group having from 1 to 200 carbon atoms.

In some embodiments $R^3$ is an alkyl group or alkenyl group having 10 to 36 carbon atoms.

In some embodiments $R^3$ is a polyisobutenyl group, preferably a polyisobutenyl group having a molecular weight of from 100 to 5000, preferably from 300 to 4000, suitably from 450 to 2500, for example from 500 to 2000 or from 600 to 1500.

In some embodiments $R^3$ is an optionally substituted alkylene phenol moiety and the tertiary amine $R^1R^2R^3N$ is the product of a Mannich reaction between an aldehyde, an optionally substituted phenol and an amine. Suitably the aldehyde is formaldehyde. The amine used to prepare the Mannich compound may be a monoamine and $R^3$ would have the structure (A):

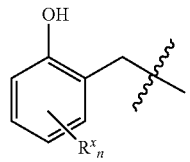

(A)

The amine used to prepare the Mannich compound may be a polyamine, including at least one tertiary amine group and $R^3$ may have the structure (B):

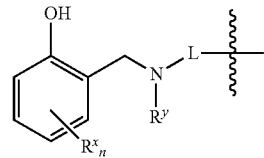

(B)

In structures (A) and (B) n is 0 to 4, preferably 1, each $R^x$ is an optionally substituted hydrocarbyl group, $R^y$ is an optionally substituted alkyl, alkenyl or aryl group; and L is a linking group.

$R^y$ and L may together form a heterocyclic group.

$R^y$ is preferably an alkyl group, preferably an unsubstituted alkyl group. $R^y$ is suitably a $C_1$ to $C_4$ alkyl group.

Preferably L is an optionally substituted alkylene group, preferably an alkylene group having 1 to 10, preferably 1 to 6 carbon atoms. More preferably L is an unsubstituted alkylene group, for example ethylene, propylene or butylene. Most preferably L is a propylene group.

In some preferred embodiments, the phenol includes an ortho-methyl substituent and a further substituent $R^x$ at the para-position.

In a preferred embodiment, n is 1 and the optionally substituted hydrocarbyl substituent R is preferably para to the hydroxyl group.

The optionally substituted hydrocarbyl substituent $R^x$ of the phenol can have 6 to 400 carbon atoms, suitably 30 to 180 carbon atoms, for example 10 or 40 to 110 carbon atoms. This hydrocarbyl substituent can be derived from an olefin or a polyolefin.

The polyolefins which can form the hydrocarbyl substituent can be prepared by polymerizing olefin monomers by well known polymerization methods and are also commercially available.

Some preferred polyolefins include polyisobutylenes having a number average molecular weight of 200 to 3000, in another instance of 400 to 2500, and in a further instance of 400 or 500 to 1500.

In some embodiments the phenol may include a lower molecular weight alkyl substituent for example a phenol which carries one or more alkyl chains having a total of less than 28 carbon atoms, preferably less than 20 carbon atoms, more preferably less than 14 carbon atoms.

A monoalkyl phenol may be preferred, suitably having from 4 to 20 carbons atoms, preferably 8 to 16 carbon atoms, for example a phenol having a $C_{12}$ alkyl substituent.

In some embodiments $R^3$ may include an ether, amide or ester group.

In some embodiments R³ includes succinimide moiety. R³ may have the formula:

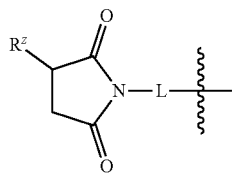

wherein R$^z$ is an optionally substituted hydrocarbyl group and L is a linking group.

In some embodiments the optionally substituted hydrocarbyl substituent R$^z$ can have 6 to 36 carbon atoms, preferably 8 to 22, for example 10 to 18 or 16 to 18 carbon atoms.

In some embodiments the optionally substituted hydrocarbyl substituent R$^z$ can have 6 to 400 carbon atoms, suitably 30 to 180 carbon atoms, for example 10 or 40 to 110 carbon atoms. This hydrocarbyl substituent can be derived from an olefin or a polyolefin.

Some preferred polyolefins include polyisobutylenes having a number average molecular weight of 200 to 3000, in another instance of 400 to 2500, and in a further instance of 400 or 500 to 1500.

Preferably L is an optionally substituted alkylene group, preferably an alkylene group having 1 to 10, preferably 1 to 6 carbon atoms. More preferably L is an unsubstituted alkylene group, for example ethylene, propylene or butylene. Most preferably L is a propylene group.

R³ may suitably be selected from an optionally substituted alkyl or alkenyl group having 1 to 10 carbon atoms; an optionally substituted hydrocarbyl group having a molecular weight of 100 to 5000; an optionally substituted alkylene phenol moiety and an optionally substituted alkylene succinimide group.

Suitable tertiary amine compounds for use as component (a) include simple alkylamino and hydroxyalkylamino compounds; trialkylamino compounds having a high molecular weight substituent; Mannich reaction products including a tertiary amine and substituted acylated amines or alcohols including a tertiary amine.

Simple alkylamino and hydroxyalkyl amino compounds are preferably compounds of formula R¹R²R³N, wherein each of R¹, R² and R³ is an alkyl group or a hydroxyalkyl group. Each of R¹, R² and R³ may be the same or different. Suitably each of R¹, R² and R³ is independently selected from an alkyl or hydroxyalkyl group having 1 to 10, preferably 1 to 6 carbon atoms, for example 1 to 4 carbon atoms. Each of R¹, R² and R³ may be independently selected from methyl, ethyl, propyl, butyl, pentyl, hexyl, hydroxymethyl, hydroxyethyl, hydroxypropyl, hydroxybutyl, hydroxypentyl and hydroxyhexyl. Component (a) may be a trialkylamine, a dialkylhydroxyalkylamine, a dihydroxyalkylalkylamine or a trihydroxyalkylamine. There are many different compounds of this type and these will be known to the person skilled in the art.

In some embodiments the amine may include alkyl or hydroxyalkyl groups which have been reacted with an epoxide compound (for example ethylene oxide or propylene oxide) to provide an ether.

Trialkylamino compounds having a high molecular weight substituent suitable for use herein are typically polyalkene-substituted amines including at least one tertiary amino group.

The polyalkene-substituted amines having at least one tertiary amino group of the present invention may be derived from an olefin polymer and an amine, for example ammonia, monoamines, polyamines or mixtures thereof. They may be prepared by a variety of methods such as those described and referred to in US 2008/0113890.

Suitably the polyalkene substituent of the polyalkene-substituted amine is derived from a polyisobutylene.

The amines that can be used to make the polyalkene-substituted amine include ammonia, monoamines, polyamines, or mixtures thereof, including mixtures of different monoamines, mixtures of different polyamines, and mixtures of monoamines and polyamines (which include diamines). The amines include aliphatic, aromatic, heterocyclic and carbocylic amines. Preferred amines are generally substituted with at least one hydrocarbyl group having 1 to about 50 carbon atoms, preferably 1 to 30 carbon atoms. Saturated aliphatic hydrocarbon radicals are particularly preferred.

The monoamines and polyamines suitably include at least one primary or secondary amine group.

The number average molecular weight of the polyalkene-substituted amines can range from 500 to 5000, or from 500 to 3000, for example from 1000 to 1500.

Any of the above polyalkene-substituted amines which are secondary or primary amines, may be alkylated to tertiary amines using alkylating agents. Suitable alkylating agents and methods using these will be known to the person skilled in the art.

Suitable Mannich reaction products having a tertiary amine for use as component (a) are described in US 2008/0052985.

The Mannich reaction product having a tertiary amine group is prepared from the reaction of an optionally substituted hydrocarbyl-substituted phenol, an aldehyde and an amine. The optionally substituted hydrocarbyl-substituted phenol is suitably as previously described herein.

Preferably the optionally substituted hydrocarbyl-substituted phenol is a polyisobutenyl-substituted phenol or a polyisobutenyl-substituted cresol.

The aldehyde used to form the Mannich detergent can have 1 to 10 carbon atoms, and is generally formaldehyde or a reactive equivalent thereof such as formalin or paraformaldehyde.

The amine used to form the Mannich detergent can be a monoamine or a polyamine.

Examples of monoamines and polyamines are known to the person skilled in the art.

Preferred polyamines are polyethylene polyamines.

In especially preferred embodiments the amine used to form the Mannich detergent comprises a diamine. Suitably it includes a primary or secondary amine which takes part in the Mannich reaction and in addition a tertiary amine.

One preferred amine is dimethylaminopropylamine.

In preferred embodiments the Mannich detergent is the product directly obtained from a Mannich reaction and comprising a tertiary amine. For example the amine may comprise a single primary or secondary amine which when reacted in the Mannich reaction forms a tertiary amine which is capable of being quaternised. Alternatively the amine may comprise a primary or secondary amine capable of taking part in the Mannich reaction and also a tertiary amine capable of being quaternised. However the Mannich detergent may comprise a compound which has been obtained from a Mannich reaction and subsequently reacted to form a tertiary amine, for example a Mannich reaction may yield a secondary amine which is then alkylated to form a tertiary amine.

Suitable preferred amines include dimethylamine and dibutylamine.

Substituted acylated amines or alcohols including a tertiary amine for use as component (a) include the reaction product of an optionally substituted hydrocarbyl-substituted acylating agent and a compound having an oxygen or nitrogen atom capable of condensing with said acylating agent and further having a tertiary amino group.

The optionally substituted hydrocarbyl substituted acylating agent is preferably a mono- or polycarboxylic acid (or reactive equivalent thereof) for example a substituted succinic, phthalic or propionic acid.

Preferred hydrocarbyl substituted acylating agents for use in the preparation of component (i) are polyisobutenyl substituted succinic acid derivatives. Preferred compounds are those having a polyisobutenyl group with a molecular weight of from 100 to 5000, preferably from 300 to 4000, suitably from 450 to 2500, for example from 500 to 2000 or from 600 to 1500.

In some preferred embodiments the tertiary amine comprises a compound formed by the reaction of an optionally substituted hydrocarbyl-substituted acylating agent and an amine of formula (II) or (III):

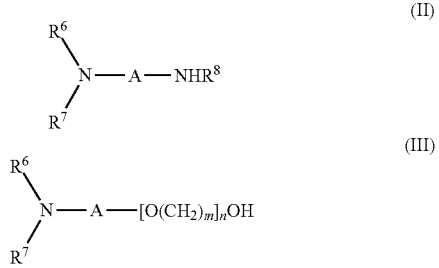

wherein $R^6$ and $R^7$ are the same or different alkyl, alkenyl or aryl groups having from 1 to 22 carbon atoms; A is a bond or is an alkylene group having from 1 to 20 carbon atoms; n is from 0 to 20; m is from 1 to 5; and $R^4$ is hydrogen or a $C_1$ to $C_{22}$ alkyl group.

The conditions of the above reaction are suitably selected to ensure that there are no free acid groups present in the tertiary amine component (a) that is formed. For example when a compound of formula (II) is reacted with a succinic acid derived acylating agent the reaction conditions or ratio of reactants are selected to ensure that the imide or diamide are formed. The monoamide is not formed. When a compound of formula (III) is reacted with a succinic acid derived acylating agent the reaction conditions or ratio of reactants are selected to ensure that the diester is formed. The monoester is not formed.

When a compound of formula (II) is used, $R^8$ is preferably hydrogen or a $C_1$ to $C_{18}$, suitably a $C_1$ to $C_{18}$ alkyl group. More preferably $R^8$ is selected from hydrogen, methyl, ethyl, propyl, butyl and isomers thereof. Most preferably $R^8$ is hydrogen.

When a compound of formula (III) is used, m is preferably 2 or 3, most preferably 2; n is preferably from 0 to 15, preferably 0 to 10, more preferably 0 to 5. Most preferably n is 0 and the compound of formula (III) is an alcohol.

Preferably the optionally substituted hydrocarbyl substituted acylating agent is reacted with a diamine compound of formula (II).

$R^6$ and $R^7$ are the same or different alkyl, alkenyl or aryl groups having from 1 to 22 carbon atoms. In some embodiments $R^6$ and $R^7$ may be joined together to form a ring structure, for example a piperidine, imidazole or morpholine moiety. Thus $R^6$ and $R^7$ may together form an aromatic and/or heterocyclic moiety. $R^6$ and $R^7$ may be branched alkyl or alkenyl groups. Each may be substituted, for example with a hydroxy or alkoxy substituent.

Preferably each of $R^6$ and $R^7$ is independently a $C_1$ to $C_{16}$ alkyl group, preferably a $C_1$ to $C_{10}$ alkyl group. $R^6$ and $R^7$ may independently be methyl, ethyl, propyl, butyl, pentyl, hexyl, heptyl, octyl, or an isomer of any of these. Preferably $R^6$ and $R^7$ is each independently $C_1$ to Ca alkyl. Preferably $R^6$ is methyl. Preferably $R^7$ is methyl.

A is a bond or alkylene group having from 1 to 20 carbon atoms. A is preferably an alkylene group having 1 to 12 carbon atoms, more preferably 1 to 8 carbon atoms, for example 2 to 6 carbon atoms or 2 to 5 carbon atoms. Most preferably A is an ethylene, propylene or butylene group, especially a propylene group.

Examples of compounds of formula (II) suitable for use herein will be known to the person skilled in the art.

In some preferred embodiments the compound of formula (II) is selected from dimethylaminopropylamine, N,N-diethyl-1,3-diaminopropane, N,N-dimethylethylenediamine, N,N-diethylethylenediamine, N,N-dibutylethylenediamine, or combinations thereof.

Examples of compounds of formula (III) suitable for use herein will be known to the person skilled in the art.

In some preferred embodiments the compound of formula (III) is selected from triisopropanolamine, 1-[2-hydroxy-ethyl]piperidine, 2-[2-(dimethylamine)ethoxy]-ethanol, N-ethyldiethanolamine, N-methyldiethanolamine, N-butyldiethanolamine, N,N-diethylaminoethanol, N,N-dimethylaminoethanol, 2-dimethylamino-2-methyl-1-propanol, or combinations thereof.

An especially preferred compound of formula (II) is dimethylaminopropylamine.

Further especially preferred tertiary amine compounds (a) are formed by the reaction of a compound including a primary amine group and a tertiary amine group and a polyisobutenyl-substituted succinic acid. One especially preferred amine compound having a primary and a tertiary amine group is dimethylaminopropylamine. The polyisobutenyl substituent preferably has a molecular weight of from 300 to 2500, suitably from 500 to 1500. Thus an especially preferred compound for use as component (a) is a polyisobutenyl-substituted succinimide prepared from dimethylaminopropylamine.

Preferred tertiary amine compounds for use as component (a) include N,N-dimethyl ethanolamine, dimethyloctadecylamine, N-methyl N,N-ditallowamine, N,N-diethyl ethanolamine, triethylamine, tripropylamine and tributylamine.

Especially preferred tertiary amines for use as component (a) include N, N-dimethylethanolamine, N, N-diethylethanolamine, triethylamine and tributylamine.

Other suitable amine that may be used as component (a) include small cyclic amines. These include for example compounds based on N-alkyl heterocycles, suitably selected from pyrolidine, piperidine, morpholine, piperazine, pyrrole, imidazole and dihydropyrrole, pyridine, pyrimidine, isoxansole and oxazole. Suitable amine starting materials of this type are described, for example, in the applicant's copending application PCT/GB2016/052312.

In some embodiments component (a) is selected from:
trialkyl amines in which each alkyl group has 1 to 6, preferably 1 to 4 carbons atoms;
dimethyl alkyl or alkenyl amines in which the alkyl or alkenyl group has 6 to 36, preferably 10 to 30 carbon atoms;
tertiary amines in which each substituent is selected from alkyl, hydroxylalkyl and hydroxyalkyloxyalkyl groups having 1 to 12, preferably 1 to 6 carbon atoms.

Preferred amines for use as component (a) are trialkylamines in which each alkyl group has 1 to 12, preferably 1 to 6 carbons atoms and in which each alkyl group may be hydroxyl substituted and/or substituted with an oxygen atom within the carbon chain.

Preferably component (a) is an amine of formula $R^1R^2R^3N$, wherein each of $R^1$, $R^2$ and $R^3$ is independently an unsubstituted alkyl group having 1 to 6 carbon atoms, a hydroxy substituted alkyl group having 1 to 6 carbon atoms or a hydroxyalkyloxyalkyl group having 1 to 6 carbon atoms.

By hydroxyalkyloxyalkyl group we mean a group of formula $HOR^aOR^b$ wherein each of $R^a$ and $R^b$ is an alkylene group. These may be formed by alkylation of a hydroxyalkyl substituent with an epoxide.

Most preferably component (a) is an amine of formula $R^1R^2R^3N$, wherein each of $R^1$, $R^2$ and $R^3$ is independently an unsubstituted alkyl group having 1 to 6 carbon atoms, or a hydroxy substituted alkyl group having 1 to 6 carbon atoms.

Component (b) used to prepare the quaternary ammonium compound of the present invention in preferred embodiments is an acid activated alkylating agent. Preferred acid-activated alkylating agents are epoxide compounds.

Any suitable epoxide compound may be used. Suitable epoxide compounds are those of formula:

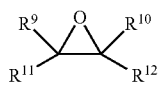

wherein each of $R^9$, $R^{10}$, $R^{11}$, $R^{12}$ is independently selected from hydrogen or an optionally substituted alkyl, alkenyl or aryl group.

In such embodiments $R^0$ as shown in formula (I) is thus suitably a group of formula:

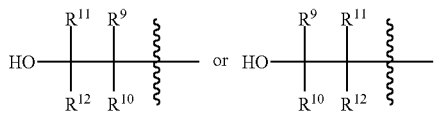

Preferably at least one of $R^9$, $R^{10}$, $R^{11}$ and $R^{12}$ is hydrogen. Preferably at least two of $R^9$, $R^{10}$, $R^{11}$ and $R^{12}$ are hydrogen. Most preferably three of $R^9$, $R^{10}$, $R^{11}$ and $R^{12}$ are hydrogen. $R^9$, $R^{10}$, $R^{11}$ and $R^{12}$ may be all hydrogen.

In the structure above and the definitions which follow $R^9$ and $R^{10}$ are interchangeable and thus when these groups are different either enantiomer or diastereomer may be used as component (b).

In the structure above and the definitions which follow $R^{11}$ and $R^{12}$ are interchangeable and thus when these groups are different either enantiomer or diastereomer may be used as component (b).

Preferably $R^9$ is hydrogen or an optionally substituted alkyl, alkenyl or aryl group, preferably having from 1 to 10, preferably from 1 to 4 carbon atoms. Preferably $R^9$ is hydrogen or an alkyl group. Most preferably $R^9$ is hydrogen.

Preferably $R^{10}$ is hydrogen or an optionally substituted alkyl, alkenyl or aryl group, preferably having from 1 to 10 carbon atoms. For example $R^{10}$ may be benzyl.

In some preferred embodiments $R^{10}$ is an optionally substituted aryl group. For example $R^{10}$ may be phenyl.

In some preferred embodiments $R^{10}$ is an optionally substituted alkyl or alkenyl group. Suitably $R^{10}$ is an alkyl group, for example an unsubstituted alkyl group. $R^{10}$ may be an alkyl group having 1 to 12, for example 1 to 8 or 1 to 4 carbon atoms.

Preferably $R^{10}$ is hydrogen or an alkyl group. Most preferably $R^{10}$ is hydrogen.

Preferably $R^{11}$ is hydrogen or an optionally substituted alkyl, alkenyl or aryl group, preferably having from 1 to 10, preferably from 1 to 4 carbon atoms. Preferably $R^{11}$ is hydrogen or an alkyl group. Most preferably $R^{11}$ is hydrogen.

Preferably $R^{12}$ is hydrogen or an optionally substituted alkyl, alkenyl or aryl group.

In some preferred embodiments $R^{12}$ is an optionally substituted aryl group. For example $R^{12}$ may be phenyl.

In some preferred embodiments $R^{12}$ is an optionally substituted alkyl or alkenyl group. $R^{12}$ may be an alkyl group, for example an unsubstituted alkyl group. $R^{12}$ may be an alkyl group having 1 to 50 carbon atoms, preferably from 1 to 30 carbon atoms, suitably 1 to 20 carbon atoms, preferably from 1 to 12 carbon atoms, for example from 1 to 8 or from 1 to 4 carbon atoms.

In some embodiments $R^{12}$ is an alkyl group having 6 to 20 carbon atoms, preferably from 8 to 16 carbon atoms.

In some embodiments $R^{12}$ is hydrogen.

In some preferred embodiments $R^{12}$ is the moiety $CH_2OR^{13}$ or $CH_2OCOR^{14}$ wherein each of $R^{13}$ and $R^{14}$ may be an optionally substituted alkyl, alkenyl or aryl group.

$R^{13}$ is preferably an optionally substituted alkyl or aryl group, preferably having from 1 to 30 carbon atoms, preferably from 1 to 20 carbon atoms, suitably from 1 to 12 carbon atoms. When $R^{13}$ is an alkyl group it may be straight-chained or branched. In some embodiments it is branched. $R^{13}$ may be an optionally substituted phenyl group.

In one embodiment $R^{13}$ is a 2-methyl phenyl group. In another embodiment $R^{13}$ is $CH_2C(CH_2CH_3)CH_2CH_2CH_2CH_3$.

$R^{14}$ may be an optionally substituted alkyl, alkenyl or aryl group.

$R^{14}$ is preferably an optionally substituted alkyl or aryl group, preferably having from 1 to 30 carbon atoms, preferably from 1 to 20 carbon atoms, suitably from 1 to 12 carbon atoms. When $R^{14}$ is an alkyl group it may be straight-chained or branched. In some preferred embodiments it is branched. $R^{14}$ may be an optionally substituted phenyl group.

In one embodiment $R^{14}$ is $C(CH_3)R_2$ wherein each R is an alkyl group. The R groups may be the same or different.

Component (b) is preferably an epoxide. The present invention therefore provides a quaternary ammonium compound which is the reaction product of:
(a) a tertiary amine of formula $R^1R^2R^3N$;
(b) an epoxide; and
(c) a compound of formula $HOOCXCOO(R^4O)R^5$ wherein $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferred epoxide compounds for use as component (b) include styrene oxide, ethylene oxide, propylene oxide, butylene oxide, epoxyhexane, octene oxide, stilbene oxide and other alkyl and alkenyl epoxides having 2 to 50 carbon atoms.

Other suitable epoxide compounds include glycidyl ethers and glycidyl esters, for example gylcidyl 2 methyl phenyl ether and the glycidyl ester of versatic acid.

Suitably component (b) may be selected from styrene oxide, ethylene oxide, propylene oxide, butylene oxide, epoxyhexane, octene oxide, stilbene oxide, 2-ethylhexyl glycidyl ether, 1,2-epoxydodecane and other alkyl and alkenyl epoxides having 2 to 50 carbon atoms.

Preferably component (b) is selected from styrene oxide, propylene oxide, butylene oxide, and 2-ethylhexyl glycidyl ether.

More preferably component (b) is selected from propylene oxide, butylene oxide and 2-ethylhexyl glycidyl ether.

The quaternary ammonium salt of the present invention includes an anion of formula $-OOCXCOO(R^4O)_nR^5$.

Suitably the quaternary ammonium salt is prepared by reaction of (a) a quaternary amine; (b) an epoxide; and (c) an acid of formula $HOOCXCOO(R^4O)_nR^5$.

The compound of formula $HOOCXCOO(R^4O)_nR^5$ is suitably a half ester which is the reaction product of an optionally substituted dicarboxylic acid or anhydride thereof and an alcohol of formula $HO(R^4O)_nR^5$.

In some embodiments the dicarboxylic acid or anhydride is unsubstituted. In preferred embodiments the additive is prepared from a hydrocarbyl substituted dicarboxylic acid or an anhydride thereof.

Suitable dicarboxylic acids include maleic acid, glutaric acid, fumaric acid, oxalic acid, malonic acid, pimelic acid, suberic acid, adipic acid, phthalic acid, succinic acid, azelaic acid, sebacic acid and dimerised fatty acids.

In one embodiment component (c) is the reaction product of an optionally substituted polycarboxylic acid or anhydride thereof selected from pyromellitic acid, malonic acid, sebacic acid and succinic acid. Suitably component (c) is an optionally substituted succinic acid or an anhydride thereof.

In some embodiments the compound of formula $HOOCXCOO(R^4O)R^5$ (component (c)) is prepared from a dimerised fatty acid. Such compounds are formed from the dimerization of unsaturated fatty acids, for example unsaturated fatty acids having 6 to 50, suitably 8 to 40, preferably 10 to 36, for example 10 to 20 carbon atoms, or 16 to 20 carbon atoms.

Such dimerised fatty acids may have 12-100 carbon atoms, preferably 16-72 carbon atoms such as 20-40 carbon atoms for example 32-40 carbon atoms.

These compound are well known in the art, particularly for their use as corrosion inhibitors. Particularly preferred dimerised fatty acids are mixtures of C36 dimer acids such as those prepared by dimerising oleic acid, linoleic acid and mixtures comprising oleic and linoleic acid, for example, tall oil fatty acids.

The quaternary ammonium compound of formula (I) includes a linking group X. Preferably X includes a hydrocarbyl substituent. Preferably X is an optionally substituted arylene or alkylene group.

In some embodiments component (c) is prepared from phthalic acid or an anhydride thereof, having the formula (A1) or (A2):

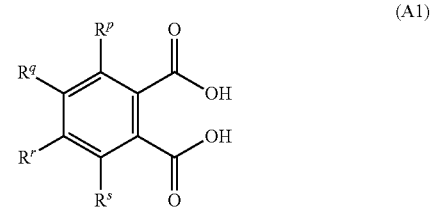

(A1)

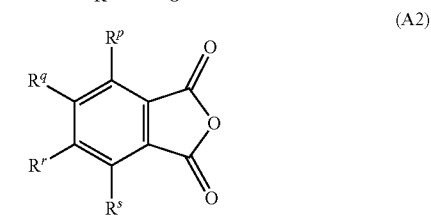

(A2)

wherein each of $R^p$, $R^q$, $R^r$ and $R^s$ is independently hydrogen or an optionally substituted hydrocarbyl group.

Preferably each is hydrogen or an optionally substituted alkyl or alkenyl group. Preferably three of $R^P$, $R^q$, $R^r$ and $R^s$ are hydrogen and the other is an optionally substituted $C_1$ to $C_{500}$ alkyl or alkenyl group, preferably a $C_2$ to $C_{100}$ alkyl or alkenyl group, preferably a $C_6$ to $C_{50}$ alkyl or alkenyl group, preferably a $C_8$ to $C_{40}$ alkyl or alkenyl group, more preferably a $C_{10}$ to $C_{36}$ alkyl or alkenyl group, preferably a $C_{12}$ to $C_{22}$ alkyl or alkenyl group, suitably a $C_{16}$ to $C_{28}$ alkyl or alkenyl group, for example a $C_{20}$ to $C_{24}$ alkyl or alkenyl group. The alkyl or alkenyl group may be straight chain or branched. Preferably $R^p$, $R^q$ and $R^s$ are hydrogen and $R^r$ is an optionally substituted alkyl or alkenyl group.

X in formula (I) is preferably an optionally substituted hydrocarbylene group. Preferably X is an optionally substituted alkylene group. Preferably X is a substituted alkylene group.

Suitably X is an alkyl or alkenyl substituted alkylene group.

Preferably X is an alkyl substituted alkylene group.

Preferably X is an alkyl substituted alkylene group wherein the alkylene group was 1 to 10, preferably 1 to 6, suitably 1 to 4, preferably 2 or 3, and most preferably 2 carbon atoms in the alkylene chain.

In some preferred embodiments X is $CH_2CHR$ or $CHRCH_2$ wherein R is an optionally substituted hydrocarbyl group.

Preferably component (c) used to prepare the quaternary ammonium salt of the present invention is the reaction product of an optionally substituted succinic acid or anhydride thereof of formula (A3) or (A4):

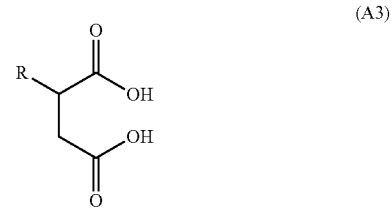

(A3)

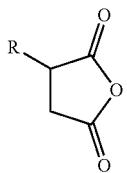
(A4)

wherein R is hydrogen or an optionally substituted hydrocarbyl group. Preferably $R^4$ is an optionally substituted alkyl or alkenyl group.

In some embodiments R is an optionally substituted $C_1$ to $C_{500}$ alkyl or alkenyl group, preferably a $C_2$ to $C_{100}$ alkyl or alkenyl group, preferably a $C_6$ to $C_{50}$ alkyl or alkenyl group, preferably a $C_8$ to $C_{40}$ alkyl or alkenyl group, more preferably a $C_{10}$ to $C_{38}$ alkyl or alkenyl group, preferably a $C_{16}$ to $C_{36}$ alkyl or alkenyl group, suitably a $C_{18}$ to $C_{32}$ alkyl or alkenyl group.

R may be substituted with one or more groups selected from halo (e.g. chloro, fluoro or bromo), nitro, hydroxy, mercapto, sulfoxy, amino, nitryl, acyl, carboxy, alkyl (e.g. $C_1$ to $C_4$ alkyl), alkoxyl (e.g. $C_1$ to $C_4$ alkoxy), amido, keto, sulfoxy and cyano.

Preferably R is an unsubstituted alkyl or alkenyl group. The substituted succinic acid or anhydrides may suitably be prepared by reacting maleic anhydride with an alkene.

In some embodiments the R has a molecular weight of from 100 to 5000, preferably from 300 to 4000, suitably from 450 to 2500, for example from 500 to 2000 or from 600 to 1500.

In some embodiments the substituted succinic acid or anhydride thereof may comprise a mixture of compounds including groups R of different lengths. In such embodiments any reference to the molecular weight of the group R relates to the number average molecular weight for the mixture.

In some embodiments R is a polyisobutenyl group, preferably having a number average molecular weight of from 100 to 5000, preferably from 200 to 2000, suitably from 220 to 1300, for example from 240 to 900.

In some embodiments R is a polyisobutenyl group having a number average molecular weight of from 400 to 700.

In some embodiments R is a polyisobutenyl group having a number average molecular weight of from 180 to 400.

In some embodiments R is a polyisobutenyl group having a number average molecular weight of from 800 to 1200.

In some embodiments R is an alkyl or alkenyl group having 6 to 40 carbon atoms, preferably 10 to 38 carbon atoms, more preferably 16 to 36 carbon atoms, suitably 18 to 26 carbon atoms, for example 20 to 24 carbon atoms.

In some embodiments R may be the residue of an internal olefin. In such embodiments the compound of formula (A3) or (A4) is suitably obtained by the reaction of maleic acid with an internal olefin.

An internal olefin as used herein means any olefin containing predominantly a non-alpha double bond that is a beta or higher olefin. Preferably such materials are substantially completely beta or higher olefins, for example containing less than 10% by weight alpha olefin, more preferably less than 5% by weight or less than 2% by weight. Typical internal olefins include Neodene 1518IO available from Shell.

Internal olefins are sometimes known as isomerised olefins and can be prepared from alpha olefins by a process of isomerisation known in the art, or are available from other sources. The fact that they are also known as internal olefins reflects that they do not necessarily have to be prepared by isomerisation.

Component (c) is the reaction product of a succinic acid or anhydride of formula (A3) or (A4) and an alcohol of formula $H—(OR^4)_n—OR^5$; wherein R is an alkyl or alkenyl group having 6 to 36 carbon atoms or a polyisobutenyl group having a number average molecular weight of from 200 to 1300.

In some especially preferred embodiments component (c) is prepared from a succinic acid or anhydride having a $C_{10}$ to $C_{30}$, preferably a $C_{20}$ to $C_{24}$ alkyl or alkenyl group.

Component (c) may have the formula (B1) or (B2):

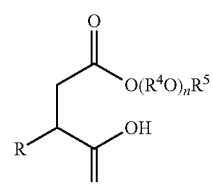
(B1)

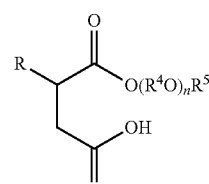
(B2)

Such a compound may be prepared by the reaction of a hydrocarbyl substituted succinic acid or anhydride with an alcohol of formula $HO(R^4O)_nR^5$.

Preferably the acid/anhydride and the alcohol are reacted in a molar ratio of from 10:1 to 1:10, preferably from 5:1 to 1:5, more preferably from 2:1 to 1:2, for example from 1.5:1 to 1:1.5.

Most preferably the acid/anhydride and the alcohol are reacted in an approximately 1:1 molar ratio, for example from 1.2:1 to 1:1.2.

Suitably n is from 0 to 30, preferably from 0 to 20, suitably from 1 to 16; $R^4$ is an alkylene group having 1 to 12, preferably 1 to 6, more preferably 2 or 3 carbon atoms; and $R^5$ is hydrogen or a $C_1$ to $C_{40}$, preferably a $C_6$ to $C_{30}$, more preferably a $C_{10}$ to $C_{20}$ alkyl group; provided n is not 0 when $R^5$ is hydrogen.

$R^5$ is an optionally substituted hydrocarbyl group.

In some embodiments n is 0 and the additive of the invention may be formed from an alcohol of formula $R^5OH$.

In such embodiments $R^5$ is suitably an optionally substituted alkyl, alkenyl or aryl group, preferably having from 1 to 60, preferably from 10 to 40 carbon atoms. Preferably $R^5$ is an optionally substituted alkyl group. In some embodiments $R^5$ is a hydroxy substituted alkyl group.

In some preferred embodiments $R^5$ is an unsubstituted alkyl group. The alkyl group may be straight chained or branched. In some embodiments $R^5$ is an optionally substituted alkyl group having 4 to 40, preferably 6 to 30, more preferably 10 to 20 carbon atoms.

In some embodiments n is 0 and component (c) is prepared from a $C_6$ to $C_{36}$, preferably a $C_8$ to $C_{30}$, more preferably a $C_{10}$ to $C_{20}$ optionally substituted alcohol.

In one embodiment component (c) is an ester of tetradecanol.

Suitable alcohols of formula $R^5OH$ for use herein include benzyl alcohol, tetradecanol, butanol, 2-butanol, isobutanol, octanol, 2-ethylhexanol, hexanol, cyclohexanol, cyclooctanol, 2-propylheptanol, 2-ethyl-1-butanol and isopropanol.

Suitable alcohols of formula $R^5OH$ for use herein are butanol and 2-ethylhexanol.

In some embodiments n is not 0 and the quaternary ammonium salt may suitably be formed from an alcohol of formula $HO(R^4O)_nR^5$.

$R^5$ is hydrogen or an optionally substituted hydrocarbyl group.

When $R^5$ is hydrogen component (c) is suitably an ester of an alkylene glycol or a polyalkylene glycol.

When $R^5$ is not hydrogen, component (c) may be formed by reaction of the optionally substituted dicarboxylic acid with an alkylene glycol or polyalkylene glycol which is subsequently reacted to form an ether or a compound of formula $HO(R^4O)_nR^5$ may be reacted with the optionally substituted dicarboxylic acid.

$R^4$ is an optionally substituted alkylene group.

In some embodiments the alcohol of formula $H-(OR)_n-OH$ has more than 2 hydroxy groups and the group R is a hydroxyl substituted alkylene group. Such a group may have 1, 2 or more hydroxyl groups.

For example in some embodiments the alcohol $H-(OR)_n-OH$ may be glycerol, penterythritol or trimethylolpropane.

Preferably $R^4$ is an unsubstituted alkylene group.

Preferably $R^4$ is an optionally substituted alkylene group having 1 to 50 carbon atoms, preferably 1 to 40 carbon atoms, preferably 1 to 30 carbon atoms, more preferably 1 to 20 carbon atoms, suitably 1 to 10 carbon atoms, for example 2 to 6 or 2 to 4 carbon atoms.

Preferably $R^4$ is an unsubstituted alkylene group having 1 to 50 carbon atoms, preferably 1 to 20, more preferably 1 to 10, suitably 2 to 6, for example 2 to 4 carbon atoms. $R^4$ may be straight chained or branched.

Suitably $R^4$ may be an ethylene, propylene, butylene, pentylene, or hexylene group. When $R^4$ has more than 2 carbon atoms any isomer may be present. Preferably $R^4$ is an ethylene or a propylene group, most preferably a propylene group.

In some embodiments in which n is 1, $R^4$ may be a group of formula $(CH_2)_x$ wherein x is from 2 to 12, preferably from 2 to 6.

In some embodiments in which n is 1, $R^4$ is a straight chain or branched alkylene group and the alcohol is selected from ethylene glycol, propylene glycol, 1,3-propanediol, 1,2-butanediol, 1,3-butanediol, 1,4-butanediol, 1,6-hexanediol and neopentyl glycol.

In some preferred embodiments $R^4$ is preferably $CR^aR^bCR^cR^d$ and the polyhydric alcohol has the formula $H-(OCR^aR^bCR^cR^d)_nOH$ wherein each of $R^a$, $R^b$, $R^c$ and $R^d$ is independently hydrogen or an optionally substituted alkyl group. Preferably each $R^a$, $R^b$, $R^c$ and $R^d$ is independently selected from hydrogen or an optionally substituted alkyl group having 1 to 20, preferably 1 to 12, more preferably 1 to 4, for example 1 to 2 carbon atoms.

Preferably each of $R^a$, $R^b$, $R^c$ and $R^d$ is independently selected from hydrogen and an unsubstituted alkyl group, preferably having 1 to 20 carbon atoms, suitably 1 to 12 carbon atoms, preferably 1 to 4 atoms, for example 1 or 2 carbon atoms. Preferably at least two of $R^a$, $R^b$, $R^c$ and $R^d$ is hydrogen, more preferably at least three of $R^a$, $R^b$, $R^c$ and $R^d$ is hydrogen.

In some embodiments $R^a$, $R^b$, $R^c$ and $R^d$ are all hydrogen and R is an ethylene group $CH_2CH_2$.

In some embodiments three of $R^a$, $R^b$, $R^c$, and $R^d$ is hydrogen and the other is an unsubstituted alkyl group having 1 to 12, preferably 1 to 4, suitably 1 to 2, and most preferably 1 carbon atoms.

In some embodiments the polyhydric alcohols used to prepare component (c) are prepared from epoxides, preferably terminal epoxides.

$R^4$ may comprise a mixture of isomers. For example when $R^4$ is propylene, the polyhydric alcohol may include moieties $-CH_2CH(CH_3)-$ and $-CH(CH_3)CH_2-$ in any order within the chain.

$R^4$ may comprise a mixture of different groups for example ethylene, propylene or butylene units. Block copolymer units are preferred in such embodiments.

$R^4$ is preferably an ethylene, propylene or butylene group. $R^4$ may be an n-propylene or n-butylene group or an isopropylene or isobutylene group. For example $R^4$ may be $-CH_2CH_2-$, $-CH_2CH(CH_3)-$, $-CH_2C(CH_3)_2$, $-CH(CH_3)CH(CH_3)-$ or $-CH_2CH(CH_2CH_3)-$.

Preferably $R^4$ is ethylene or propylene. More preferably $R^4$ is $-CH_2CH_2-$ or $-CH(CH_3)CH_2-$. Most preferably $R^4$ is $-CH(CH_3)CH_2-$.

In some embodiments n is at least 1. Preferably n is from 1 to 100, preferably from 1 to 50, more preferably from 1 to 30, more preferably from 1 to 24, preferably from 1 to 20, suitably from 1 to 16, preferably from 1 to 14.

In some embodiments n is from 4 to 10, for example from 6 to 8.

In some embodiments n is from 1 to 6, suitably from 2 to 5, for example 3 or 4.

In some embodiments n is from 8 to 16, for example from 11 to 14.

In some embodiments component (c) is prepared from a polyhydric alcohol of formula $HO(R^4O)H$ or an ether thereof of formula $HO(R^4O)_nR^5$.

Preferably the acid/anhydride and the alcohol are reacted in a molar ratio of from 10:1 to 1:10, preferably from 5:1 to 1:5, more preferably from 2:1 to 1:2, for example from 1.5:1 to 1:1.5.

Most preferably the acid/anhydride and the alcohol are reacted in an approximately 1:1 molar ratio, for example from 1.2:1 to 1:1.2.

In some embodiments the polyhydric alcohol may be a polypropylene glycol having a number average molecular weight of 425.

In some embodiments the polyhydric alcohol may be selected from triethylene glycol, tetraethyelene glycol, propylene glycol, dipropylene glycol and tripropylene glycol.

In some embodiments the polyhydric alcohol is selected from ethylene glycol, propylene glycol and oligomers or polymers thereof.

In some embodiments the polyhydric alcohol may be a polypropylene glycol having a number average molecular weight of 725.

The skilled person will appreciate that commercial sources of alcohols of formula $H-(OR^4)_n-OH$ will often contain mixtures of compounds, for example in which n may be between 6 and 10.

Commercial sources of substituted succinic acids and anhydrides may also contain mixtures of compounds, for example including different compounds with substituents having 20 to 24 carbon atoms.

In some preferred embodiments $R^5$ is hydrogen.

In some embodiments $R^5$ is hydrogen, n is 1, and R is a straight chain or branched alkylene group. In such embodiments the alcohol of formula $HO(R^4O)_nR^5$ is selected from ethylene glycol, propylene glycol, 1,3-propanediol, 1,2-butanediol, 1,3-butanediol, 1,4-butanediol, 1,6-hexanediol and neopentyl glycol.

In some embodiments $R^5$ is not hydrogen, n is not 0 and the additive of the invention is prepared from an ether of a polyhydric alcohol, for example an ether of a polyethylene glycol, a polypropylene glycol, triethylene glycol, tetraethylene glycol, propylene glycol, dipropylene glycol or tripropylene glycol.

In some embodiments in which n is not 0, $R^5$ is an optionally substituted alkyl, alkenyl or aryl group, suitably an optionally substituted alkyl or alkenyl group. Preferably $R^5$ has from 4 to 50 carbon atoms, preferably 4 to 40 carbon atoms, more preferably from 10 to 30 carbon atoms. $R^5$ may be straight chain or branched. Preferably $R^5$ is straight chain.

In some embodiments $R^5$ is a substituted alkyl or alkenyl group, suitably a substituted alkyl group. Suitably substituents are hydroxy and ester groups.

Suitably $R^5$ is an unsubstituted alkyl or alkenyl group. Preferably $R^5$ is an alkyl group, preferably an unsubstituted alkyl group.

Suitably $R^5$ is selected from hydrogen, and an alkyl group having from 1 to 40, preferably 6 to 30, more preferably 10 to 20 carbon atoms.

In some embodiments n is from 10 to 40, preferably 15 to 30, more preferably 20 to 25; $R^2$ is ethylene or propylene, most preferably propylene; and $R^5$ is a $C_6$ to $C_{30}$, preferably a $C_{10}$ to $C_{20}$ alkyl group.

In some embodiments component (c) is the reaction product of an optionally substituted polycarboxylic acid or anhydride thereof selected from pyromellitic acid, malonic acid, sebacic acid and succinic acid; and an alcohol of formula $HO(R^4O)_nR^5$, the alcohol being selected from:
 ethylene glycol, propylene glycol and oligomers or polymers thereof; alkane diols having 1 to 12, preferably 3 to 6 carbon atoms; sugar alcohols or ethers thereof; and alkanols having 1 to 30, preferably 6 to 25 carbon atoms.

In some embodiments component (c) is the reaction product of an optionally substituted polycarboxylic acid or anhydride thereof selected from pyromellitic acid and succinic acid; and an alcohol of formula $HO(R^4O)_nR^5$ wherein the alcohol is selected from:
 ethylene glycol, diethylene glycol, triethylene glycol, tetraethylene glycol, propylene glycol, dipropylene glycol, tripropylene glycol, tetrapropylene glycol, trehalose, 1,3-propanediol, 1,2-butanediol, 1,3-butanediol, 1,4-butanediol, 1,6-hexanediol, neopentyl glycol, a polyethylene or polypropylene glycol having a number average molecular weight of 300 to 1200; or a C1 to C30 ether thereof; and
 benzyl alcohol, tetradecanol, butanol, 2-butanol, isobutanol, octanol, 2-ethylhexanol, hexanol, cyclohexanol, cyclooctanol, 2-propylheptanol, 2-ethyl-1-butanol and isopropanol.

In some embodiments component (c) is the reaction product of a succinic acid or anhydride of formula (A3) or (A4) and an alcohol of formula $HO(R^4O)_nR^5$; wherein $R^2$ is an alkyl or alkenyl group having 6 to 36 carbon atoms or a polyisobutenyl group having a number average molecular weight of from 200 to 1300; wherein the alcohol of formula $HO(R^4O)_nR^5$ is selected from:
 ethylene glycol, diethylene glycol, triethylene glycol, tetraethylene glycol, propylene glycol, dipropylene glycol, tripropylene glycol, tetrapropylene glycol, trehalose, sorbitol, glycerol, pentaerythritol, trimethylolpropane, 1,3-propanediol, 1,2-butanediol, 1,3-butanediol, 1,4-butanediol, 1,6-hexanediol, neopentyl glycol and a polyethylene or polypropylene glycol having a number average molecular weight of 300 to 1200; or a C6 to C24 ether thereof; and
 benzyl alcohol, tetradecanol, butanol, 2-butanol, isobutanol, octanol, 2-ethylhexanol, hexanol, cyclohexanol, cyclooctanol, 2-propylheptanol, 2-ethyl-1-butanol and isopropanol.

In some embodiments component (c) used to prepare the quaternary ammonium salt of the present invention is the reaction product of a succinic acid or anhydride thereof having an alkyl or alkenyl substituent having 6 to 36 carbon atoms and a polypropylene glycol (or a $C_1$ to $C_{36}$ alkyl ether thereof) having a number average molecular weight of 300 to 800.

In some embodiments component (c) is the reaction product of a succinic acid or anhydride thereof having an alkyl or alkenyl substituent having 6 to 36 carbon atoms and a polyhydric alcohol (or a $C_1$ to $C_{36}$ alkyl ether thereof) selected from ethylene glycol, diethylene glycol, triethylene glycol, tetraethylene glycol, propylene glycol, dipropylene glycol, tripropylene glycol and tetrapropylene glycol.

In some embodiments component (c) is the reaction product of a succinic acid or anhydride thereof having an alkyl or alkenyl substituent having 6 to 36 carbon atoms and a polyhydric alcohol (or a $C_1$ to $C_{36}$ alkyl ether thereof) selected from glycerol, pentaerythritol and trimethyolpropane.

In some embodiments component (c) is the reaction product of a succinic acid or anhydride having a $C_6$ to $C_{36}$, preferably a $C_{10}$ to $C_{30}$, more preferably a $C_{20}$ to $C_{24}$ alkyl or alkenyl substituent and a polyethylene or polypropylene glycol (or a $C_1$ to $C_{36}$ alkyl ether thereof) having 4 to 16, preferably 6 to 8 alkoxy groups.

In some embodiments component (c) is the reaction product of a succinic acid or anhydride having a $C_{10}$ to $C_{30}$, preferably a $C_{20}$ to $C_{24}$ alkyl or alkenyl substituent and an alcohol of formula $R^5OH$ wherein $R^5$ is a $C_6$ to $C_{30}$, preferably a $C_{10}$ to $C_{20}$ alkyl group.

In some embodiments component (c) is the reaction product of a succinic acid or anhydride thereof having an alkyl or alkenyl substituent having 6 to 36 carbon atoms and a polyethylene glycol (or a $C_1$ to $C_{36}$ alkyl ether thereof) having a number average molecular weight of 200 to 800.

In some embodiments component (c) is the reaction product of a polyisobutenyl substituted succinic acid or anhydride thereof having a PIB substituent with a number average molecular weight of 200 to 2500 and a polypropylene glycol (or a $C_1$ to $C_{36}$ alkyl ether thereof) having a number average molecular weight of 300 to 800.

In some embodiments component (c) is the reaction product of a polyisobutenyl substituted succinic acid or anhydride thereof having a PIB substituent with a number average molecular weight of 200 to 2500 and a polyhydric alcohol (or a $C_1$ to $C_{36}$ alkyl ether thereof) selected from ethylene glycol, diethylene glycol, triethylene glycol, tetraethylene glycol, propylene glycol, dipropylene glycol, tripropylene glycol and tetrapropylene glycol.

In some embodiments component (c) is the reaction product of a polyisobutenyl substituted succinic acid or anhydride thereof having a PIB substituent with a number average molecular weight of 200 to 2500 and a polyhydric alcohol (or a $C_1$ to $C_{36}$ alkyl ether thereof) selected from glycerol, pentaerythritol and trimethyolpropane.

In some embodiments component (c) is a the reaction product of polyisobutenyl substituted succinic acid or anhydride thereof having a PIB substituent with a number average molecular weight of 200 to 2500 and a polyethylene glycol (or a $C_1$ to $C_{36}$ alkyl ether thereof) having a number average molecular weight of 200 to 800.

In some embodiments component (c) is the reaction product of a polyisobutenyl substituted succinic acid or anhydride thereof having a PIB substituent with a number average molecular weight of 200 to 2500 a polyethylene or polypropylene glycol (or a $C_1$ to $C_{36}$ alkyl ether thereof) having 4 to 16, preferably 6 to 8 alkoxy groups.

For avoidance of doubt component (c) may comprise a mixture of compounds. Compounds that may be present include mixtures formed by reacting a mixture of different polyhydric alcohols with a polycarboxylic acid and/or mixtures formed by reacting a polyhydric alcohol with a mixture of polycarboxylic acids and/or compounds formed by reacting a mixture of polyhydric alcohols with a mixture of carboxylic acids. Such mixtures may also include mixtures of initially pure fully formed ester compounds.

In an especially preferred embodiment component (c) is the reaction product of a succinic acid or anhydride having a $C_{20}$ to $C_{24}$ alkyl or alkenyl substituent and an alcohol selected from polypropylene glycol having a number average molecular weight of 300 to 800, 2-ethylhexanol and butanol.

In preferred embodiments the quaternary ammonium compound of the present invention is the reaction product of:
(a) a tertiary amine of formula $R^1R^2R^3N$ wherein each of, $R^1$, $R^2$ and $R^3$ is independently an optionally substituted alkyl group having 1 to 12 carbon atoms;
(b) an epoxide selected from styrene oxide, ethylene oxide, propylene oxide, butylene oxide, epoxyhexane, octene oxide, stilbene oxide, 2-ethylhexyl glycidyl ether, 1,2-epoxydodecane and other alkyl and alkenyl epoxides having 2 to 50 carbon atoms; and
(c) a compound of formula $HOOCXCOO\text{—}(R^4O)_n\text{—}R^5$ wherein X is $CH_2CHR$ or $CHRCH_2$ wherein R is an optionally substituted hydrocarbyl group; and
  n is more than 1, $R^4$ is an ethylene or propylene group and $R^5$ is hydrogen; or
  n is 0 or and $R^5$ is a $C_1$ to $C_{20}$ alkyl group.

In more preferred embodiments the quaternary ammonium compound of the present invention is the reaction product of:
(a) a tertiary amine of formula $R^1R^2R^3N$ wherein each of, $R^1$, $R^2$ and $R^3$ is independently an alkyl or hydroxyalkyl group having 1 to 6 carbon atoms;
(b) an epoxide selected from propylene oxide, butylene oxide and 2-ethylhexyl glycidyl ether; and
(c) a compound of formula $HOOCXCOO\text{—}(R^4O)_n\text{—}R^5$ which is the reaction product of a succinic acid or anhydride having a $C_{20}$ to $C_{24}$ alkyl or alkenyl substituent and an alcohol selected from polypropylene glycol having a number average molecular weight of 300 to 800, 2-ethylhexanol and butanol.

According to a third aspect of the present invention there is provided a composition comprising a quaternary ammonium compound of formula (I):

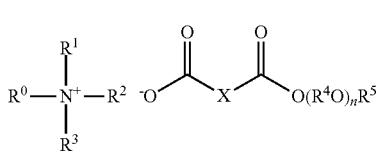

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferred features of the third aspect are as defined in relation to the first and second aspects.

In some embodiments the composition of the third aspect is an additive composition comprising a quaternary ammonium salt of the first aspect and a diluent or carrier.

The additive composition may be an additive composition for lubricating oil.

Preferably the additive composition is an additive composition for a fuel composition, preferably a diesel fuel composition.

The quaternary ammonium compound is suitably present in the additive composition in an amount of from 1 to 99 wt %, for example from 1 to 75 wt %.

The additive composition may comprise a mixture of two or more quaternary ammonium compounds of the present invention. In such embodiments the above amounts suitably refer to the total amount of all such compounds present in the composition.

The additive composition may include one or more further additives. These may be selected from antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, metal deactivators, odour masks, drag reducers and conductivity improvers.

In some preferred embodiments the additive composition includes one or more further nitrogen-containing detergents.

The third aspect of the present invention may provide a fuel or lubricating oil composition comprising a quaternary ammonium salt of the first aspect.

In some embodiments the present invention provides a lubricating composition comprising an oil of lubricating viscosity and as an additive a quaternary ammonium salt of formula (I):

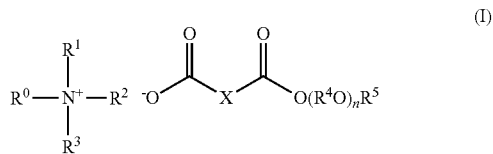

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

In some preferred embodiments the third aspect of the present invention provides a fuel composition comprising as an additive a quaternary ammonium salt of formula (I):

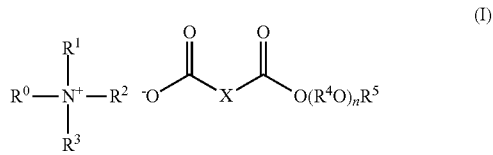

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

The present invention may further provide a method of preparing a fuel composition, the method comprising preparing a quaternary ammonium salt of the first aspect, and mixing the quaternary ammonium salt into the fuel.

The fuel composition of the present invention is preferably a diesel fuel composition.

Suitably the quaternary ammonium salt additive is present in the diesel fuel composition in an amount of at least 0.1 ppm, preferably at least 1 ppm, more preferably at least 5 ppm, suitably at least 10 ppm, preferably at least 20 ppm, for example at least 30 ppm or at least 50 ppm.

Suitably the quaternary ammonium salt additive is present in the diesel fuel composition in an amount of less than 10000 ppm, preferably less than 1000 ppm, preferably less than 500 ppm, preferably less than 300 ppm, for example less than 250 ppm.

In some embodiments the quaternary ammonium salt additive is present in the diesel fuel composition in an amount of suitably less than 200 ppm, for example less than 150 ppm.

Suitably the quaternary ammonium salt additive is present in the diesel fuel in an amount of from 80 to 130 ppm.

In this specification any reference to ppm is to parts per million by weight.

The diesel fuel compositions of the present invention may comprise a mixture of two or more quaternary ammonium salt additives. In such embodiments the above amounts refer to the total amounts of all such additives present in the composition.

The use of mixtures may arise due to the availability of starting materials or a particular mixture may be deliberately selected to use in order to achieve a benefit. For example, a particular mixture may lead to improvements in handling, a general improvement in performance or a synergistic improvement in performance.

In this specification any reference to "an additive" or "the additive" of the invention includes embodiments in which a single additive compound is present and embodiments in which two or more additive compounds are present. In embodiments in which two or more compounds are present the mixtures may be present due to a mixture of starting materials being used to prepare the additive compounds (e.g. a mixture of polyhydric alcohols and/or a mixture of polycarboxylic acids and/or a mixture of tertiary amines and/or a mixture of quaternising agents). Alternatively and/or additionally two or more pre-formed compounds of formula (I) may be mixed into a composition, for example a fuel or lubricating composition.

The quaternary ammonium salt additives may be added to diesel fuel at any convenient place in the supply chain. For example, the additives may be added to fuel at the refinery, at a distribution terminal or after the fuel has left the distribution terminal. If the additive is added to the fuel after it has left the distribution terminal, this is termed an aftermarket application. Aftermarket applications include such circumstances as adding the additive to the fuel in the delivery tanker, directly to a customer's bulk storage tank, or directly to the end user's vehicle tank. Aftermarket applications may include supplying the fuel additive in small bottles suitable for direct addition to fuel storage tanks or vehicle tanks.

By diesel fuel we include any fuel suitable for use in a diesel engine either for road use or non-road use. This includes but is not limited to fuels described as diesel, marine diesel, heavy fuel oil, industrial fuel oil, etc.

The diesel fuel composition used in the present invention may comprise a petroleum-based fuel oil, especially a middle distillate fuel oil. Such distillate fuel oils generally boil within the range of from 110° C. to 500° C., e.g. 150° C. to 400° C. The diesel fuel may comprise atmospheric distillate or vacuum distillate, cracked gas oil, or a blend in any proportion of straight run and refinery streams such as thermally and/or catalytically cracked and hydro-cracked distillates.

The diesel fuel composition may comprise non-renewable Fischer-Tropsch fuels such as those described as GTL (gas-to-liquid) fuels, CTL (coal-to-liquid) fuels and OTL (oil sands-to-liquid).

The diesel fuel composition may comprise a renewable fuel such as a biofuel composition or biodiesel composition.

The diesel fuel composition may comprise 1st generation biodiesel. First generation biodiesel contains esters of, for example, vegetable oils, animal fats and used cooking fats. This form of biodiesel may be obtained by transesterification of oils, for example rapeseed oil, soybean oil, canola oil, safflower oil, palm oil, corn oil, peanut oil, cotton seed oil, tallow, coconut oil, physic nut oil (Jatropha), sunflower seed oil, used cooking oils, hydrogenated vegetable oils or any mixture thereof, with an alcohol, usually a monoalcohol, usually in the presence of a catalyst.

The diesel fuel composition may comprise second generation biodiesel. Second generation biodiesel is derived from renewable resources such as vegetable oils and animal fats and processed, often in the refinery, using, for example, hydroprocessing such as the H-Bio process developed by Petrobras. Second generation biodiesel may be similar in properties and quality to petroleum based fuel oil streams, for example renewable diesel produced from vegetable oils, animal fats etc. and marketed by ConocoPhillips as Renewable Diesel and by Neste as NExBTL.

The diesel fuel composition may comprise third generation biodiesel. Third generation biodiesel utilises gasification and Fischer-Tropsch technology including those described as BTL (biomass-to-liquid) fuels. Third generation biodiesel does not differ widely from some second generation biodiesel, but aims to exploit the whole plant (biomass) and thereby widens the feedstock base.

The diesel fuel composition may contain blends of any or all of the above diesel fuel compositions.

In some embodiments the diesel fuel composition may be a blended diesel fuel comprising bio-diesel. In such blends the bio-diesel may be present in an amount of, for example, up to 0.5%, up to 1%, up to 2%, up to 3%, up to 4%, up to 5%, up to 10%, up to 20%, up to 30%, up to 40%, up to 50%, up to 60%, up to 70%, up to 80%, up to 90%, up to 95% or up to 99%.

In some embodiments the fuel composition may comprise neat biodiesel.

In some preferred embodiments the fuel composition comprises at least 5 wt % biodiesel.

In some embodiments the fuel composition may comprise a neat GTL fuel.

In some embodiments the diesel fuel composition may comprise a secondary fuel, for example ethanol. Preferably however the diesel fuel composition does not contain ethanol.

The diesel fuel composition used in the present invention may contain a relatively high sulphur content, for example greater than 0.05% by weight, such as 0.1% or 0.2%.

However, in preferred embodiments the diesel fuel composition has a sulphur content of at most 0.05% by weight, more preferably of at most 0.035% by weight, especially of at most 0.015%. Fuels with even lower levels of sulphur are also suitable such as, fuels with less than 50 ppm sulphur by weight, preferably less than 20 ppm, for example 10 ppm or less.

The diesel fuel composition of the present invention preferably comprises at least 5 wt % biodiesel and less than 50 ppm sulphur.

The quaternary ammonium salt additives of the present invention have been found to be effective at controlling deposits in fuel and lubricating compositions.

The present invention may provide the use of a quaternary ammonium compound of the first aspect as an additive for fuel or lubricating oil compositions.

The present invention may provide the use of a quaternary ammonium compound of the first aspect as a deposit control additive for fuel or lubricating oil compositions.

The present invention may provide the use of a quaternary ammonium compound of the first aspect as a deposit control additive for lubricating oil compositions.

The present invention may provide the use of a quaternary ammonium compound of the first aspect as a deposit control additive for fuel compositions.

The present invention may provide the use of a quaternary ammonium compound of the first aspect as a deposit control additive for diesel fuel compositions.

According to a fourth aspect of the present invention there is provided the use of a quaternary ammonium compound of formula (I):

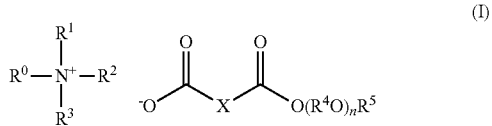

(I)

wherein $R^0$, $R^1$, $R^2$ and $R^3$ is each individually an optionally substituted alkyl, alkenyl or aryl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen as an additive in a fuel or lubricant composition.

Preferred features of the fourth aspect are as defined in relation to the first, second and third aspects.

The use of the fourth aspect preferably relates to use of the quaternary ammonium salt as a fuel additive, preferably a diesel fuel additive.

Preferably the use of the fourth aspect relates to the use of the quaternary ammonium salt of the first aspect as a detergent additive.

The fourth aspect of the present invention may provide the use of a quaternary ammonium compound of formula (I) to improve the performance of an engine. The use is suitably achieved when a composition comprising the quaternary ammonium compound is combusted in the engine.

Preferably the engine is a diesel engine.

According to a fifth aspect of the present invention there is provided a method of improving the performance of an engine, the method comprising combusting in the engine a fuel composition comprising as an additive a quaternary ammonium compound of formula (I):

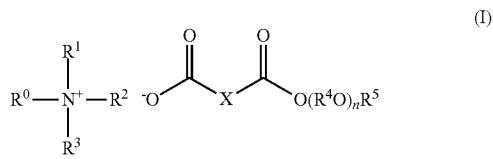

(I)

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen.

Preferred features of the fifth aspect of the invention are as defined in relation to the first, second, third and fourth aspects.

The method of the fifth aspect preferably involves combusting in the engine a composition of the third aspect.

The fifth aspect of the invention relates to a method of improving the performance of an engine.

Preferably the engine is a diesel engine.

Most preferably the engine is a direct injection diesel engine.

The present invention relates to improving the performance of diesel engines by combusting diesel fuel compositions comprising a quaternary ammonium salt additive.

Preferably the improvement in performance of the engine is achieved by combatting deposits in the engine.

In preferred embodiments the fifth aspect of the present invention relates to a method of combatting deposits in an engine, preferably a diesel engine.

The method may be achieved by combusting in the engine a composition quaternary ammonium salt additive which functions as a detergent.

Thus the present invention may provide a method of combatting deposits in a diesel engine, the method comprising combusting in the engine a fuel composition comprising as an additive a quaternary ammonium salt of the first aspect.

Suitably the use of the fourth aspect of an engine improves the performance of an engine, preferably a diesel engine. This improvement in performance may, for example, be achieved by combatting deposits in the engine.

The fourth aspect of the present invention relates to the use of the quaternary ammonium salt additive as a detergent.

References herein to improving performance and/or combating deposits may apply to either the fourth and/or the fifth aspect of the invention.

The quaternary ammonium salt additives used in the present invention have been found to be particularly effective in modern diesel engines having a high pressure fuel system. Some features of engines of this type have been previously described herein.

Suitably the present invention combats deposits and/or improves performance of a diesel engine having a high pressure fuel system. Suitably the diesel engine has a pressure in excess of 1350 bar ($1.35\times10^8$ Pa). It may have a pressure of up to 2000 bar ($2\times10^8$ Pa) or more.

Two non-limiting examples of such high pressure fuel systems are: the common rail injection system, in which the fuel is compressed utilizing a high-pressure pump that supplies it to the fuel injection valves through a common rail; and the unit injection system which integrates the high-pressure pump and fuel injection valve in one assembly, achieving the highest possible injection pressures exceeding 2000 bar ($2 \times 10^8$ Pa). In both systems, in pressurising the fuel, the fuel gets hot, often to temperatures around 100° C., or above.

In common rail systems, the fuel is stored at high pressure in the central accumulator rail or separate accumulators prior to being delivered to the injectors. Often, some of the heated fuel is returned to the low pressure side of the fuel system or returned to the fuel tank. In unit injection systems the fuel is compressed within the injector in order to generate the high injection pressures. This in turn increases the temperature of the fuel.

In both systems, fuel is present in the injector body prior to injection where it is heated further due to heat from the combustion chamber. The temperature of the fuel at the tip of the injector can be as high as 250-350° C.

Thus the fuel is stressed at pressures from 1350 bar ($1.35 \times 10^8$ Pa) to over 2000 bar ($2 \times 10^8$ Pa) and temperatures from around 100° C. to 350° C. prior to injection, sometimes being recirculated back within the fuel system thus increasing the time for which the fuel experiences these conditions.

A common problem with diesel engines is fouling of the injector, particularly the injector body, and the injector nozzle. Fouling may also occur in the fuel filter. Injector nozzle fouling occurs when the nozzle becomes blocked with deposits from the diesel fuel. Fouling of fuel filters may be related to the recirculation of fuel back to the fuel tank. Deposits increase with degradation of the fuel. Deposits may take the form of carbonaceous coke-like residues, lacquers or sticky or gum-like residues. Diesel fuels become more and more unstable the more they are heated, particularly if heated under pressure. Thus diesel engines having high pressure fuel systems may cause increased fuel degradation. In recent years the need to reduce emissions has led to the continual redesign of injection systems to help meet lower targets. This has led to increasingly complex injectors and lower tolerance to deposits.

The problem of injector fouling may occur when using any type of diesel fuels. However, some fuels may be particularly prone to cause fouling or fouling may occur more quickly when these fuels are used. For example, fuels containing biodiesel and those containing metallic species may lead to increased deposits.

When injectors become blocked or partially blocked, the delivery of fuel is less efficient and there is poor mixing of the fuel with the air. Over time this leads to a loss in power of the engine, increased exhaust emissions and poor fuel economy.

Deposits are known to occur in the spray channels of the injector, leading to reduced flow and power loss. As the size of the injector nozzle hole is reduced, the relative impact of deposit build up becomes more significant. Deposits are also known to occur at the injector tip. Here, they affect the fuel spray pattern and cause less effective combustion and associated higher emissions and increased fuel consumption.

In addition to these "external" injector deposits in the nozzle hole and at the injector tip which lead to reduced flow and power loss, deposits may occur within the injector body causing further problems. These deposits may be referred to as internal diesel injector deposits (or IDIDs). IDIDs occur inside the injector on the critical moving parts. They can hinder the movement of these parts affecting the timing and quantity of fuel injection. Since modern diesel engines operate under very precise conditions these deposits can have a significant impact on performance.

IDIDs cause a number of problems, including power loss and reduced fuel economy due to less than optimal fuel metering and combustion. Initially the user may experience cold start problems and/or rough engine running. These deposits can lead to more serious injector sticking. This occurs when the deposits stop parts of the injector from moving and thus the injector stops working. When several or all of the injectors stick the engine may fail completely.

The CEC have recently introduced an Internal Diesel Injector Deposit Test, CEC F-110-16, to discriminate between fuels that differ in their ability to produce IDID in direct injection common rail diesel engines.

As mentioned above, the problem of injector fouling may be more likely to occur when using fuel compositions comprising metal species. Various metal species may be present in fuel compositions. This may be due to contamination of the fuel during manufacture, storage, transport or use or due to contamination of fuel additives. Metal species may also be added to fuels deliberately. For example, transition metals are sometimes added as fuel borne catalysts, for example to improve the performance of diesel particulate filters.

Problems of injector sticking may occur when metal or ammonium species, particularly sodium species, react with carboxylic acid species in the fuel.

Sodium contamination of diesel fuel and the resultant formation of carboxylate salts is believed to be a major cause of injector sticking.

In some embodiments the diesel fuel compositions used in the present invention comprise sodium and/or calcium. Suitably they comprise sodium. The sodium and/or calcium is typically present in a total amount of from 0.01 to 50 ppm, preferably from 0.05 to 5 ppm preferably 0.1 to 2 ppm such as 0.1 to 1 ppm.

Other metal-containing species may also be present as a contaminant, for example through the corrosion of metal and metal oxide surfaces by acidic species present in the fuel or from lubricating oil. In use, fuels such as diesel fuels routinely come into contact with metal surfaces for example, in vehicle fueling systems, fuel tanks, fuel transportation means etc. Typically, metal-containing contamination may comprise transition metals such as zinc, iron and copper; Group I or Group II metals and other metals such as lead.

The presence of metal containing species may give rise to fuel filter deposits and/or external injector deposits including injector tip deposits and/or nozzle deposits.

In addition to metal-containing contamination which may be present in diesel fuels there are circumstances where metal-containing species may deliberately be added to the fuel. For example, as is known in the art, metal-containing fuel-borne catalyst species may be added to aid with the regeneration of particulate traps. The presence of such catalysts may also give rise to injector deposits when the fuels are used in diesel engines having high pressure fuel systems.

Metal-containing contamination, depending on its source, may be in the form of insoluble particulates or soluble compounds or complexes. Metal-containing fuel-borne catalysts are often soluble compounds or complexes or colloidal species.

In some embodiments, the diesel fuel may comprise metal-containing species comprising a fuel-borne catalyst. Preferably, the fuel borne catalyst comprises one or more metals selected from iron, cerium, platinum, manganese, Group I and Group II metals e.g., calcium and strontium. Most preferably the fuel borne catalyst comprises a metal selected from iron and cerium.

In some embodiments, the diesel fuel may comprise metal-containing species comprising zinc. Zinc may be present in an amount of from 0.01 to 50 ppm, preferably from 0.05 to 5 ppm, more preferably 0.1 to 1.5 ppm.

Typically, the total amount of all metal-containing species in the diesel fuel, expressed in terms of the total weight of metal in the species, is between 0.1 and 50 ppm by weight, for example between 0.1 and 20 ppm, preferably between 0.1 and 10 ppm by weight, based on the weight of the diesel fuel.

It is advantageous to provide a diesel fuel composition which prevents or reduces the occurrence of deposits in a diesel engine. In some embodiments such deposits may include "external" injector deposits such as deposits in and around the nozzle hole and at the injector tip. In some preferred embodiments the deposits include "internal" injector deposits or IDIDs. Such fuel compositions may be considered to perform a "keep clean" function i.e. they prevent or inhibit fouling. It is also be desirable to provide a diesel fuel composition which would help clean up deposits of these types. Such a fuel composition which when combusted in a diesel engine removes deposits therefrom thus effecting the "clean-up" of an already fouled engine.

As with "keep clean" properties, "clean-up" of a fouled engine may provide significant advantages. For example, superior clean up may lead to an increase in power and/or an increase in fuel economy. In addition removal of deposits from an engine, in particular from injectors may lead to an increase in interval time before injector maintenance or replacement is necessary thus reducing maintenance costs.

Although for the reasons mentioned above deposits in injectors is a particular problem found in modern diesel engines with high pressure fuels systems, it is desirable to provide a diesel fuel composition which also provides effective detergency in older traditional diesel engines such that a single fuel supplied at the pumps can be used in engines of all types.

It is also desirable that fuel compositions reduce the fouling of vehicle fuel filters. It is useful to provide compositions that prevent or inhibit the occurrence of fuel filter deposits i.e. provide a "keep clean" function. It is useful to provide compositions that remove existing deposits from fuel filter deposits i.e. provide a "clean up" function. Compositions able to provide both of these functions are especially useful.

The method of the present invention is particularly effective at combatting deposits in a modern diesel engine having a high pressure fuel system.

Such diesel engines may be characterised in a number of ways.

Such engines are typically equipped with fuel injection equipment meeting or exceeding "Euro 5" emissions legislation or equivalent legislation in the US or other countries.

Such engines are typically equipped with fuel injectors having a plurality of apertures, each aperture having an inlet and an outlet.

Such engines may be characterised by apertures which are tapered such that the inlet diameter of the spray-holes is greater than the outlet diameter.

Such modern engines may be characterised by apertures having an outlet diameter of less than 500 µm, preferably less than 200 µm, more preferably less than 150 µm, preferably less than 100 µm, most preferably less than 80 µm or less.

Such modern diesel engines may be characterised by apertures where an inner edge of the inlet is rounded.

Such modern diesel engines may be characterised by the injector having more than one aperture, suitably more than 2 apertures, preferably more than 4 apertures, for example 6 or more apertures.

Such modern diesel engines may be characterised by an operating tip temperature in excess of 250° C.

Such modern diesel engines may be characterised by a fuel injection system which provides a fuel pressure of more than 1350 bar, preferably more than 1500 bar, more preferably more than 2000 bar. Preferably, the diesel engine has fuel injection system which comprises a common rail injection system.

The method of the present invention preferably combats deposits in an engine having one or more of the above-described characteristics.

The use of the present invention preferably improves the performance of an engine. This improvement in performance is suitably achieved by reducing deposits in the engine.

The first aspect of the present invention relates to a method of combating deposits in a diesel engine. Combating deposits may involve reducing or the preventing of the formation of deposits in an engine compared to when running the engine using unadditised fuel. Such a method may be regarded as achieving "keep clean" performance.

Combating deposits may involve the removal of existing deposits in an engine. This may be regarded as achieving "clean up" performance.

In especially preferred embodiments the method of the fifth aspect and the use of the fourth aspect of the present invention may be used to provide "keep clean" and "clean up" performance.

As explained above deposits may occur at different places within a diesel engine, for example a modern diesel engine.

The present invention is particularly useful in the prevention or reduction or removal of internal deposits in injectors of engines operating at high pressures and temperatures in which fuel may be recirculated and which comprise a plurality of fine apertures through which the fuel is delivered to the engine. The present invention finds utility in engines for heavy duty vehicles and passenger vehicles. Passenger vehicles incorporating a high speed direct injection (or HSDI) engine may for example benefit from the present invention.

The present invention may also provide improved performance in modern diesel engines having a high pressure fuel system by controlling external injector deposits, for example those occurring in the injector nozzle and/or at the injector tip. The ability to provide control of internal injector deposits and external injector deposits is a useful advantage of the present invention.

Suitably the present invention may reduce or prevent the formation of external injector deposits. It may therefore provide "keep clean" performance in relation to external injector deposits.

Suitably the present invention may reduce or remove existing external injector deposits. It may therefore provide "clean up" performance in relation to external injector deposits.

Suitably the present invention may reduce or prevent the formation of internal diesel injector deposits. It may therefore provide "keep clean" performance in relation to internal diesel injector deposits.

Suitably the present invention may reduce or remove existing internal diesel injector deposits. It may therefore provide "clean up" performance in relation to internal diesel injector deposits.

The present invention may also combat deposits on vehicle fuel filters. This may include reducing or preventing the formation of deposits ("keep clean" performance) or the reduction or removal of existing deposits ("clean up" performance).

The removal or reduction of IDIDs according to the present invention will lead to an improvement in performance of the engine.

The improvement in performance of the diesel engine system may be measured by a number of ways. Suitable methods will depend on the type of engine and whether "keep clean" and/or "clean up" performance is measured.

An improvement in "keep clean" performance may be measured by comparison with a base fuel. "Clean up" performance can be observed by an improvement in performance of an already fouled engine.

The effectiveness of fuel additives is often assessed using a controlled engine test.

In Europe the Co-ordinating European Council for the development of performance tests for transportation fuels, lubricants and other fluids (the industry body known as CEC), has developed a test for additives for modern diesel engines such as HSDI engines. The CEC F-98-08 test is used to assess whether diesel fuel is suitable for use in engines meeting new European Union emissions regulations known as the "Euro 5" regulations. The test is based on a Peugeot DW10 engine using Euro 5 injectors, and is commonly referred to as the DW10B test. This test measures power loss in the engine due to deposits on the injectors, and is further described in example 4.

Preferably the use of the fuel composition of the present invention leads to reduced deposits in the DW10B test. For "keep clean" performance a reduction in the occurrence of deposits is preferably observed.

For "clean up" performance removal of deposits is preferably observed. The DW10B test is used to measure the power loss in modern diesel engines having a high pressure fuel system.

Suitably the use of a fuel composition of the present invention may provide a "keep clean" performance in modern diesel engines, that is the formation of deposits in the injectors of these engines may be inhibited or prevented. Preferably this performance is such that a power loss of less than 5%, preferably less than 2% is observed after 32 hours as measured by the DW10B test.

Suitably the use of a fuel composition of the present invention may provide a "clean up" performance in modern diesel engines that is, deposits on the injectors of an already fouled engine may be removed. Preferably this performance is such that the power of a fouled engine may be returned to within 1% of the level achieved when using clean injectors within 16 hours, preferably 12 hours, more preferably 8 hours as measured in the DW10B test.

In some preferred embodiments, clean up may also provide a power increase. Thus a fouled engine may be treated to remove the existing deposits and provide an additional power gain.

Clean injectors can include new injectors or injectors which have been removed and physically cleaned, for example in an ultrasound bath.

The CEC have also developed a new test, commonly known as the DW10C which assesses the ability of a fuel composition to prevent the formation of IDIDs that lead to injector sticking. This test is described in example 5. A modified version of this test adapted to measure clean up, is described in example 6.

The DW10C test may be used to measure the "keep clean" or "clean up" performance of an engine.

In some embodiments the present invention provides a "keep clean" performance in relation to the formation of IDIDs. Such performance may be illustrated by achieving a merit score of at least 7 as measured by the DW10C test, preferably at least 8, more preferably at least 9.

In some embodiments a merit score of at least 9.3 may be achieved, for example at least 9.4, at least 9.5, at least 9.6 or at least 9.7.

In some embodiments the present invention provides a "clean-up" performance in relation to IDIDs, whereby existing IDIDs may be removed. Such a performance is illustrated in the examples.

The diesel fuel compositions of the present invention may also provide improved performance when used with traditional diesel engines. Preferably the improved performance is achieved when using the diesel fuel compositions in modern diesel engines having high pressure fuel systems and when using the compositions in traditional diesel engines. This is important because it allows a single fuel to be provided that can be used in new engines and older vehicles.

For older engines an improvement in performance may be measured using the XUD9 test. This test is described in relation to example 5.

Suitably the use of a fuel composition of the present invention may provide a "keep clean" performance in traditional diesel engines, that is the formation of deposits on the injectors of these engines may be inhibited or prevented. Preferably this performance is such that a flow loss of less than 50%, preferably less than 30% is observed after 10 hours as measured by the XUD-9 test.

Suitably the use of a fuel composition of the present invention may provide a "clean up" performance in traditional diesel engines, that is deposits on the injectors of an already fouled engine may be removed. Preferably this performance is such that the flow loss of a fouled engine may be reduced by 10% or more within 10 hours as measured in the XUD-9 test.

The benefits provided by the present invention mean that engines need to be serviced less frequently, leading to cost savings and an increase in maintenance intervals.

Preferably the method and use of the present invention provide an improvement in the performance of a diesel engine. This improvement in performance is suitably selected from one or more of:
 a reduction in power loss of the engine;
 a reduction in external diesel injector deposits;
 a reduction in internal diesel injector deposits;
 an improvement in fuel economy;
 a reduction in fuel filter deposits;
 a reduction in emissions; and
 an increase in maintenance intervals.

The additives of the present invention may provide a further benefit in addition to those listed above. For example the additive may provide lubricity benefits and/or corrosion inhibition and/or cold flow improvement.

The diesel fuel compositions of the present invention may include one or more further additives such as those which are commonly found in diesel fuels. These include, for example, antioxidants, dispersants, detergents, metal deactivating compounds, wax anti-settling agents, cold flow improvers, cetane improvers, dehazers, stabilisers, demulsifiers, antifoams, corrosion inhibitors, lubricity improvers, dyes, markers, combustion improvers, metal deactivators, odour masks, drag reducers and conductivity improvers.

Examples of suitable amounts of each of these types of additives will be known to the person skilled in the art.

In some embodiments the combination of an additive of the invention and a further additive may provide synergistic improvement in performance.

For example the use of a quaternary ammonium salt additive of the invention in combination with a cold flow improver may provide an unexpected improvement in detergency and/or cold flow performance compared with the performance of the individual additives used alone.

In some embodiments the use of a quaternary ammonium salt additive of the present invention may enable a lower treat rate of cold flow improver to be used.

For example the use of a quaternary ammonium salt additive of the invention in combination with a corrosion inhibitor may provide an unexpected improvement in detergency and/or corrosion inhibition compared with the performance of the individual additives used alone.

In some embodiments the use of a quaternary ammonium salt additive of the present invention may enable a lower treat rate of corrosion inhibitor to be used.

For example the use of a quaternary ammonium salt additive of the invention in combination with a lubricity improver may provide an unexpected improvement in detergency and/or lubricity compared with the performance of the individual additives used alone.

In some embodiments the use of a quaternary ammonium salt additive of the present invention may enable a lower treat rate of lubricity improver to be used.

In some preferred embodiments the diesel fuel composition of the present invention comprises one or more further detergents. Nitrogen-containing detergents are preferred.

The one or more further detergents may provide a synergistic benefit such that an improved performance is observed when using the combination of a quaternary ammonium salt additive of the invention and a nitrogen-containing detergent compared to the use of an equivalent amount of either additive alone.

The use of a combination of a quaternary ammonium salt additive and a nitrogen-containing detergent may also combat deposits and improve performance in a traditional diesel engine.

The one or more further detergents may be selected from:
(i) a quaternary ammonium salt additive which is not a compound of formula (I);
(ii) the product of a Mannich reaction between an aldehyde, an amine and an optionally substituted phenol;
(iii) the reaction product of a carboxylic acid-derived acylating agent and an amine;
(iv) the reaction product of a carboxylic acid-derived acylating agent and hydrazine;
(v) a salt formed by the reaction of a carboxylic acid with di-n-butylamine or tri-n-butylamine;
(vi) the reaction product of a hydrocarbyl-substituted dicarboxylic acid or anhydride and an amine compound or salt which product comprises at least one amino triazole group; and
(vii) a substituted polyaromatic detergent additive.

Preferably one or more further detergents are selected from one or more of:
(i) a quaternary ammonium salt additive which is not a compound of formula (I);
(ii) the product of a Mannich reaction between an aldehyde, an amine and an optionally substituted phenol; and
(iii) the reaction product of a carboxylic acid-derived acylating agent and an amine.

The ratio of the quaternary ammonium salt additive to the nitrogen containing detergent is suitable from 5:1 to 1:5, preferably from 2:1 to 1:2.

In some embodiments the diesel fuel composition further comprises (i) a quaternary ammonium salt additive which is not a compound of formula (I).

The quaternary ammonium salt additive is suitably the reaction product of a nitrogen-containing species having at least one tertiary amine group and a quaternising agent.

The nitrogen containing species may be selected from:
(x) the reaction product of a hydrocarbyl-substituted acylating agent and a compound comprising at least one tertiary amine group and a primary amine, secondary amine or alcohol group;
(y) a Mannich reaction product comprising a tertiary amine group; and
(z) a polyalkylene substituted amine having at least one tertiary amine group.

Examples of quaternary ammonium salt and methods for preparing the same are described in the following patents, which are hereby incorporated by reference, US2008/0307698, US2008/0052985, US2008/0113890 and US2013/031827.

The preparation of some suitable quaternary ammonium salt additives in which the nitrogen-containing species includes component (x) is described in WO 2006/135881 and WO2011/095819.

Component (y) is a Mannich reaction product having a tertiary amine. The preparation of quaternary ammonium salts formed from nitrogen-containing species including component (y) is described in US 2008/0052985.

The preparation of quaternary ammonium salt additives in which the nitrogen-containing species includes component (z) is described for example in US 2008/0113890.

To form the quaternary ammonium salt additive (i) the nitrogen-containing species having a tertiary amine group is reacted with a quaternising agent.

The quaternising agent may suitably be selected from esters and non-esters.

Preferred quaternising agents for use herein include dimethyl oxalate, methyl 2-nitrobenzoate, methyl salicylate and styrene oxide or propylene oxide optionally in combination with an additional acid.

An especially preferred additional quaternary ammonium salt for use herein is formed by reacting methyl salicylate or dimethyl oxalate with the reaction product of a polyisobutylene-substituted succinic anhydride having a PIB number average molecular weight of 700 to 1300 and dimethylaminopropylamine.

Other suitable quaternary ammonium salts include quaternised terpolymers, for example as described in US2011/0258917; quaternised copolymers, for example as described in US2011/0315107; and the acid-free quaternised nitrogen compounds disclosed in US2012/0010112.

Further suitable quaternary ammonium compounds for use in the present invention include the quaternary ammonium compounds described in the applicants copending applications WO2011095819, WO2013/017889, WO2015/011506, WO2015/011507, WO2016/016641 and PCT/GB2016/052312.

In some embodiments the diesel fuel composition used in the present invention comprises from 1 to 500 ppm, preferably 50 to 250 ppm of the quaternary ammonium salt additive of the present invention and from 1 to 500 ppm, preferably 50 to 250 ppm of a further quaternary ammonium additive (i).

In some embodiments the diesel fuel composition comprises further (ii) the product of a Mannich reaction between an aldehyde, an amine and an optionally substituted phenol. This Mannich reaction product is suitably not a quaternary ammonium salt.

Preferably the aldehyde component used to prepare the Mannich additive is an aliphatic aldehyde. Preferably the aldehyde has 1 to 10 carbon atoms. Most preferably the aldehyde is formaldehyde.

Suitable amines for use in preparing the Mannich additive include monoamines and polyamines. One suitable monoamine is butylamine.

The amine used to prepare the Mannich additive is preferably a polyamine. This may be selected from any compound including two or more amine groups. Preferably the polyamine is a polyalkylene polyamine, preferably a polyethylene polyamine. Most preferably the polyamine comprises tetraethylenepentamine or ethylenediamine.

The optionally substituted phenol component used to prepare the Mannich additive may be substituted with 0 to 4 groups on the aromatic ring (in addition to the phenol OH). For example it may be a hydrocarbyl-substituted cresol. Most preferably the phenol component is a mono-substituted phenol. Preferably it is a hydrocarbyl substituted phenol. Preferred hydrocarbyl substituents are alkyl substituents having 4 to 28 carbon atoms, especially 10 to 14 carbon atoms. Other preferred hydrocarbyl substituents are polyalkenyl substituents. Such polyisobutenyl substituents having a number average molecular weight of from 400 to 2500, for example from 500 to 1500.

In some embodiments the diesel fuel composition of the present invention comprises from 1 to 500 ppm, preferably 50 to 250 ppm of a quaternary ammonium salt of the first aspect and from 1 to 500 ppm, preferably 50 to 250 ppm of a Mannich additive (ii).

In some embodiments the diesel fuel composition further comprises (iii) the reaction product of a carboxylic acid-derived acylating agent and an amine.

These may also be referred to herein in general as acylated nitrogen-containing compounds.

Suitable acylated nitrogen-containing compounds may be made by reacting a carboxylic acid acylating agent with an amine and are known to those skilled in the art.

Preferred hydrocarbyl substituted acylating agents are polyisobutenyl succinic anhydrides.

These compounds are commonly referred to as "PIBSAs" and are known to the person skilled in the art.

Conventional polyisobutenes and so-called "highly-reactive" polyisobutenes are suitable for use in the invention.

Especially preferred PIBSAs are those having a PIB molecular weight (Mn) of from 300 to 2800, preferably from 450 to 2300, more preferably from 500 to 1300.

In preferred embodiments the reaction product of the carboxylic acid derived acylating agent and an amine includes at least one primary or secondary amine group.

A preferred acylated nitrogen-containing compound for use herein is prepared by reacting a poly(isobutene)-substituted succinic acid-derived acylating agent (e.g., anhydride, acid, ester, etc.) wherein the poly(isobutene) substituent has a number average molecular weight (Mn) of between 170 to 2800 with a mixture of ethylene polyamines having 2 to about 9 amino nitrogen atoms, preferably about 2 to about 8 nitrogen atoms, per ethylene polyamine and about 1 to about 8 ethylene groups. These acylated nitrogen compounds are suitably formed by the reaction of a molar ratio of acylating agent:amino compound of from 10:1 to 1:10, preferably from 5:1 to 1:5, more preferably from 2:1 to 1:2 and most preferably from 2:1 to 1:1. In especially preferred embodiments, the acylated nitrogen compounds are formed by the reaction of acylating agent to amino compound in a molar ratio of from 1.8:1 to 1:1.2, preferably from 1.6:1 to 1:1.2, more preferably from 1.4:1 to 1:1.1 and most preferably from 1.2:1 to 1:1. Acylated amino compounds of this type and their preparation are well known to those skilled in the art and are described in for example EP0565285 and U.S. Pat. No. 5,925,151.

In some preferred embodiments the composition comprises a detergent of the type formed by the reaction of a polyisobutene-substituted succinic acid-derived acylating agent and a polyethylene polyamine. Suitable compounds are, for example, described in WO2009/040583.

In some embodiments the diesel fuel composition of the present invention comprises from 1 to 500 ppm, preferably 50 to 250 ppm of a quaternary ammonium salt of the first aspec and from 1 to 500 ppm, preferably 50 to 250 ppm of an additive which is the reaction product of an acylating agents and an amine (iii).

In some embodiments the diesel fuel composition comprises (iv) the reaction product of a carboxylic acid-derived acylating agent and hydrazine.

Suitably the additive comprises the reaction product between a hydrocarbyl-substituted succinic acid or anhydride and hydrazine.

Preferably, the hydrocarbyl group of the hydrocarbyl-substituted succinic acid or anhydride comprises a $C_8$-$C_{36}$ group, preferably a $C_8$-$C_{18}$ group. Alternatively, the hydrocarbyl group may be a polyisobutylene group with a number average molecular weight of between 200 and 2500, preferably between 800 and 1200.

Hydrazine has the formula $NH_2$—$NH_2$ Hydrazine may be hydrated or non-hydrated. Hydrazine monohydrate is preferred.

The reaction between the hydrocarbyl-substituted succinic acid or anhydride and hydrazine produces a variety of products, such as is disclosed in US 2008/0060259.

In some embodiments the diesel fuel composition further comprises (v) a salt formed by the reaction of a carboxylic acid with di-n-butylamine or tri-n-butylamine. Exemplary compounds of this type are described in US 2008/0060608.

Such additives may suitably be the di-n-butylamine or tri-n-butylamine salt of a fatty acid of the formula [R' (COOH)$_x$]y, where each R' is a independently a hydrocarbon group of between 2 and 45 carbon atoms, and x is an integer between 1 and 4.

In a preferred embodiment, the carboxylic acid comprises tall oil fatty acid (TOFA).

Further preferred features of additives of this type are described in EP1900795.

In some embodiments the diesel fuel composition further comprises (vi) the reaction product of a hydrocarbyl-substituted dicarboxylic acid or anhydride and an amine compound or salt which product comprises at least one amino triazole group.

Further preferred features of additive compounds of this type are as defined in US2009/0282731.

In some embodiments the diesel fuel composition further comprises (vii) a substituted polyaromatic detergent additive.

One preferred compound of this type is the reaction product of an ethoxylated naphthol and paraformaldehyde which is then reacted with a hydrocarbyl substituted acylating agent.

Further preferred features of these detergents are described in EP1884556.

Any feature of the invention may be combined with any other feature as appropriate.

The invention will now be further described with reference to the following non-limiting examples. In the examples which follow the values given in parts per million (ppm) for treat rates denote active agent amount, not the amount of a formulation as added, and containing an active agent. All parts per million are by weight.

Example 1

Additive A1, a quaternary ammonium salt additive of the invention was prepared as follows:

(a) A mixture of alkenes having 20 to 24 carbon atoms was heated with 1.2 molar equivalents of maleic anhydride. On completion of the reaction excess maleic anhydride was removed by distillation. The anhydride value of the substituted succinic anhydride product was measured as 2.591 mmolg$^{-1}$.

This product was then heated with one molar equivalent of polypropylene glycol having a number average molecular weight of 425, and the reaction was monitored by FTIR to provide the half ester/half acid product.

(b) 1 molar equivalent of diethyl ethanolamine was reacted with 1.5 molar equivalents of butylene oxide and 6 molar equivalents of water at 60° C. in toluene for 10 hours in the presence of the half ester/half acid provided in the step (a) to form a quaternary ammonium compound. Volatiles were removed in vacuo.

Compounds A2 to A21 detailed in table 1 were prepared by an analogous method.

TABLE 1

| Compound | R | H-(OR$^4$)n-OR$^5$ | Amine | Epoxide |
|---|---|---|---|---|
| A1 | C20-24 | polypropylene glycol Mn425 | Diethyl ethanolamine | Butylene oxide |
| A2 | C20-24 | polypropylene glycol Mn425 | Dimethyl ethanolamine | Butylene oxide |
| A3 | C20-24 | polypropylene glycol Mn425 | Triethylamine | Butylene oxide |
| A4 | C20-24 | polypropylene glycol Mn425 | Tributylamine | Butylene oxide |
| A5 | C20-24 | tripropylene glycol | Dimethyl ethanolamine | Butylene oxide |
| A6 | C20-24 | tripropylene glycol | Diethyl ethanolamine | Butylene oxide |
| A7 | C20-24 | tripropylene glycol | Triethylamine | Butylene oxide |
| A8 | C20-24 | tripropylene glycol | Tributylamine | Butylene oxide |
| A9 | C20-24 | triethyleneglycol | Dimethyl ethanolamine | Butylene oxide |
| A10 | C20-24 | triethyleneglycol | Diethyl ethanolamine | Butylene oxide |
| A11 | C20-24 | triethyleneglycol | Triethylamine | Butylene oxide |
| A12 | C20-24 | triethyleneglycol | Tributylamine | Butylene oxide |
| A13 | C20-24 | polypropylene glycol Mn725 | Dimethyl ethanolamine | Butylene oxide |
| A14 | C20-24 | polypropylene glycol Mn725 | Diethyl ethanolamine | Butylene oxide |
| A15 | C20-24 | polypropylene glycol Mn725 | Triethylamine | Butylene oxide |
| A16 | C20-24 | polypropylene glycol Mn725 | Tributylamine | Butylene oxide |
| A17 | C20-24 | Tetra-ethyleneglycol | Dimethyl ethanolamine | Butylene oxide |
| A18 | C20-24 | Tetra-ethyleneglycol | Diethyl ethanolamine | Butylene oxide |
| A19 | C20-24 | tetra-ethyleneglycol | Triethylamine | Butylene oxide |
| A20 | C20-24 | tetra-ethyleneglycol | Tributylamine | Butylene oxide |
| A21 | C20-24 | poly-ethyleneglycol Mn400 | Dimethyl ethanolamine | Butylene oxide |
| A22 | C20-24 | 2-Ethylhexanol | N,N-diethyl ethanolamine | Butylene oxide |
| A23 | C20-24 | Butanol | N,N-diethyl ethanolamine | Butylene oxide |
| A24 | C20-24 | Poly(ethylene glycol) Mn400 | 2-[2-(Dimethyl-amino)ethoxy]ethanol | 1,2-epoxydodecane |
| A25 | C20-24 | Poly(ethylene glycol) Mn400 | N,N-dimethyl Benzylamine | 2-Ethylhexyl Glycidyl Ether |
| A26 | C20-24 | Poly(ethylene glycol) Mn400 | N,N-dimethyl ethanolamine | 1,2-epoxydodecane |
| A27 | C20-24 | Poly(ethylene glycol) Mn400 | N,N-dimethyl ethanolamine | Styrene Oxide |
| A28 | C20-24 | Poly(ethylene glycol) Mn400 | N,N-Dimethyl octadecylamine | 2-Ethylhexyl Glycidyl Ether |
| A29 | C20-24 | Poly(ethylene glycol) Mn400 | N,N-Dimethyl octadecylamine | Butylene oxide |
| A30 | C20-24 | Poly(ethylene glycol) Mn400 | N,N-Dimethyl octadecylamine | 1,2-epoxydodecane |
| A31 | C20-24 | Poly(ethylene glycol) Mn400 | N,N-Dimethyl octadecylamine | Styrene Oxide |
| A32 | C20-24 | Poly(propylene glycol) Mn425 | N,N-dimethyl Benzylamine | 2-Ethylhexyl Glycidyl Ether |
| A33 | C20-24 | Poly(propylene glycol) Mn425 | N,N-dimethyl Benzylamine | Butylene oxide |
| A34 | C20-24 | Poly(propylene glycol) Mn425 | N,N-dimethyl Benzylamine | Styrene Oxide |
| A35 | C20-24 | Poly(propylene glycol) Mn425 | N,N-dimethyl ethanolamine | 1,2-epoxydodecane |
| A36 | C20-24 | Poly(propylene glycol) Mn425 | N,N-Dimethyl octadecylamine | 2-Ethylhexyl Glycidyl Ether |
| A37 | C20-24 | Poly(propylene glycol) Mn425 | N,N-Dimethyl octadecylamine | Butylene oxide |
| A38 | C20-24 | Poly(propylene glycol) Mn425 | N,N-Dimethyl octadecylamine | Styrene Oxide |
| A39 | C20-24 | Tetradecanol | N,N-diethyl ethanolamine | Butylene oxide |
| A40 | C20-24 | Tri(propylene glycol) | 2-[2-(Dimethyl-amino)ethoxy]ethanol | 2-Ethylhexyl Glycidyl Ether |
| A41 | C20-24 | Tri(propylene glycol) | 2-[2-(Dimethyl-amino)ethoxy]ethanol | 1,2-epoxydodecane |
| A42 | C20-24 | Tri(propylene glycol) | 2-[2-(Dimethyl-amino)ethoxy]ethanol | Styrene Oxide |
| A43 | C20-24 | Tri(propylene glycol) | N,N-dimethyl Benzylamine | 2-Ethylhexyl Glycidyl Ether |
| A44 | C20-24 | Tri(propylene glycol) | N,N-dimethyl Benzylamine | Butylene oxide |
| A45 | C20-24 | Tri(propylene glycol) | N,N-dimethyl Benzylamine | 1,2-epoxydodecane |
| A46 | C20-24 | Tri(propylene glycol) | N,N-dimethyl Benzylamine | Styrene Oxide |
| A47 | C20-24 | Tri(propylene glycol) | N,N-dimethyl ethanolamine | 1,2-epoxydodecane |
| A48 | C20-24 | Tri(propylene glycol) | N,N-Dimethyl octadecylamine | 2-Ethylhexyl Glycidyl Ether |
| A49 | C20-24 | Tri(propylene glycol) | N,N-Dimethyl octadecylamine | Butylene oxide |
| A50 | C20-24 | Tri(propylene glycol) | N,N-Dimethyl octadecylamine | 1,2-epoxydodecane |
| A51 | C20-24 | Tri(propylene glycol) | N,N-Dimethyl octadecylamine | Styrene Oxide |
| A52 | 1000PIB | Tri(propylene glycol) | N,N-dimethyl ethanolamine | 1,2-epoxydodecane |

Example 2

Diesel fuel compositions were prepared by dosing additives to aliquots all drawn from a common batch of RF06 base fuel.

The compositions were tested in a screening test which correlates with performance at combatting IDIDs as measured in the DW10C test.

In this test a fuel composition is tested using a Jet Fuel Thermal Oxidation Test equipment. In this modified test 800 ml of fuel is flowed over a heated tube at pressures of approximately 540 psi. The test duration is 2.5 hours. At the end of the test the amount of deposit obtained on the tube is compared to a reference value.

The value shown in table 2 is the percentage reduction in deposit thickness compared to base fuel.

TABLE 2

| Compound | ppm active | Average thickness (% reduction) |
| --- | --- | --- |
| A1 (inventive) | 120 | 95 |
| A3 (inventive) | 120 | 97 |
| A4 (inventive) | 120 | 95 |
| A6 (inventive) | 120 | 84 |
| A7 (inventive) | 120 | 98 |
| A8 (inventive) | 120 | 97 |
| A10 (inventive) | 120 | 92 |
| A11 (inventive) | 120 | 92 |
| A12 (inventive) | 120 | 91 |
| A14 (inventive) | 120 | 99 |
| A15 (inventive) | 120 | 91 |
| A16 (inventive) | 120 | 98 |
| A19 (inventive) | 120 | 91 |
| A20 (inventive) | 120 | 91 |
| A22 (inventive) | 120 | 81 |
| A23 (inventive) | 120 | 91 |
| A24 (inventive) | 120 | 98 |
| A25 (inventive) | 120 | 80 |
| A26 (inventive) | 120 | 98 |
| A27 (inventive) | 120 | 81 |
| A28 (inventive) | 120 | 79 |
| A29 (inventive) | 120 | 90 |
| A30 (inventive) | 120 | 97 |
| A31 (inventive) | 120 | 100 |
| A32 (inventive) | 120 | 95 |
| A33 (inventive) | 120 | 92 |
| A34 (inventive) | 120 | 90 |
| A35 (inventive) | 120 | 94 |
| A36 (inventive) | 120 | 91 |
| A37 (inventive) | 120 | 99 |
| A38 (inventive) | 120 | 96 |
| A40 (inventive) | 120 | 85 |
| A41 (inventive) | 120 | 82 |
| A42 (inventive) | 120 | 85 |
| A43 (inventive) | 120 | 90 |
| A44 (inventive) | 120 | 97 |
| A45 (inventive) | 120 | 99 |
| A46 (inventive) | 120 | 78 |
| A47 (inventive) | 120 | 97 |
| A48 (inventive) | 120 | 87 |
| A49 (inventive) | 120 | 91 |
| A50 (inventive) | 120 | 99 |
| A51 (inventive) | 120 | 78 |
| C1 (comparative) | 120 | 0 |
| C2 (comparative) | 120 | 2 |

Comparative additive C1 is dodecenyl substituted succinic acid.

Comparative additive C2 is a polyisobutenyl (PIB) substituted succinic acid where the PIB has a number average molecular weight of 1000.

Table 3 below shows the specification for RF06 base fuel.

TABLE 3

| | | Limits | | |
| --- | --- | --- | --- | --- |
| Property | Units | Min | Max | Method |
| Cetane Number | | 52.0 | 54.0 | EN ISO 5165 |
| Density at 15° C. | kg/m$^3$ | 833 | 837 | EN ISO 3675 |
| Distillation | | | | |
| 50% v/v Point | ° C. | 245 | — | |
| 95% v/v Point | ° C. | 345 | 350 | |
| FBP | ° C. | — | 370 | |
| Flash Point | ° C. | 55 | — | EN 22719 |
| Cold Filter Plugging Point | ° C. | — | −5 | EN 116 |
| Viscosity at 40° C. | mm$^2$/sec | 2.3 | 3.3 | EN ISO 3104 |
| Polycyclic Aromatic Hydrocarbons | % m/m | 3.0 | 6.0 | IP 391 |
| Sulphur Content | mg/kg | — | 10 | ASTM D 5453 |
| Copper Corrosion | | — | 1 | EN ISO 2160 |
| Conradson Carbon Residue on 10% Dist. Residue | % m/m | — | 0.2 | EN ISO 10370 |
| Ash Content | % m/m | — | 0.01 | EN ISO 6245 |
| Water Content | % m/m | — | 0.02 | EN ISO 12937 |
| Neutralisation (Strong Acid) Number | mg KOH/g | — | 0.02 | ASTM D 974 |
| Oxidation Stability | mg/mL | — | 0.025 | EN ISO 12205 |
| HFRR (WSD1, 4) | μm | — | 400 | CEC F-06-A-96 |
| Fatty Acid Methyl Ester | | prohibited | | |

Example 3

The performance of fuel compositions of example 2 in modern diesel engines having a high pressure fuel system may be tested according to the CECF-98-08 DW 10 method. This is referred to herein as the DW10B test.

The engine of the injector fouling test is the PSA DW10BTED4. In summary, the engine characteristics are:

Design: Four cylinders in line, overhead camshaft, turbocharged with EGR

Capacity: 1998 cm$^3$

Combustion chamber: Four valves, bowl in piston, wall guided direct injection

Power: 100 kW at 4000 rpm

Torque: 320 Nm at 2000 rpm

Injection system: Common rail with piezo electronically controlled 6-hole injectors.

Max. pressure: 1600 bar (1.6×10$^8$ Pa). Proprietary design by SIEMENS VDO

Emissions control: Conforms with Euro IV limit values when combined with exhaust gas post-treatment system (DPF)

This engine was chosen as a design representative of the modern European high-speed direct injection diesel engine capable of conforming to present and future European emissions requirements. The common rail injection system uses a highly efficient nozzle design with rounded inlet edges and conical spray holes for optimal hydraulic flow. This type of nozzle, when combined with high fuel pressure has allowed advances to be achieved in combustion efficiency, reduced noise and reduced fuel consumption, but are sensitive to influences that can disturb the fuel flow, such as deposit formation in the spray holes. The presence of these deposits causes a significant loss of engine power and increased raw emissions.

The test is run with a future injector design representative of anticipated Euro V injector technology.

It is considered necessary to establish a reliable baseline of injector condition before beginning fouling tests, so a sixteen hour running-in schedule for the test injectors is specified, using non-fouling reference fuel.

Full details of the CEC F-98-08 test method can be obtained from the CEC. The coking cycle is summarised below.

1. A warm up cycle (12 minutes) according to the following regime:

| Step | Duration (minutes) | Engine Speed (rpm) | Torque (Nm) |
|---|---|---|---|
| 1 | 2 | idle | <5 |
| 2 | 3 | 2000 | 50 |
| 3 | 4 | 3500 | 75 |
| 4 | 3 | 4000 | 100 |

2. 8 hrs of engine operation consisting of 8 repeats of the following cycle

| Step | Duration (minutes) | Engine Speed (rpm) | Load (%) | Torque (Nm) | Boost Air After IC (° C.) |
|---|---|---|---|---|---|
| 1 | 2 | 1750 | (20) | 62 | 45 |
| 2 | 7 | 3000 | (60) | 173 | 50 |
| 3 | 2 | 1750 | (20) | 62 | 45 |
| 4 | 7 | 3500 | (80) | 212 | 50 |
| 5 | 2 | 1750 | (20) | 62 | 45 |
| 6 | 10 | 4000 | 100 | * | 50 |
| 7 | 2 | 1250 | (10) | 20 | 43 |
| 8 | 7 | 3000 | 100 | * | 50 |
| 9 | 2 | 1250 | (10) | 20 | 43 |
| 10 | 10 | 2000 | 100 | * | 50 |
| 11 | 2 | 1250 | (10) | 20 | 43 |
| 12 | 7 | 4000 | 100 | * | 50 |

* for expected range see CEC method CEC-F-98-08

3. Cool down to idle in 60 seconds and idle for 10 seconds
4. 4 hrs soak period

The standard CEC F-98-08 test method consists of 32 hours engine operation corresponding to 4 repeats of steps 1-3 above, and 3 repeats of step 4. ie 56 hours total test time excluding warm ups and cool downs.

Example 4

The ability of additives of the invention to remove 'Internal Diesel Injector Deposits' (IDIDs) may be measured according to the test method CEC F-110-16, available from the Co-ordinating European Council. The test uses the PSA DW10C engine.

The engine characteristics as follows:

| | |
|---|---|
| Design: | Four cylinders in line, overhead camshaft, variable geometry turbocharger with EGR |
| Capacity: | 1997 cm$^3$ |
| Combustion chamber: | Four valves, bowl in piston, direct injection |
| Power: | 120 kW @ 3750 rpm |
| Torque: | 340 Nm @ 2000 rpm |

-continued

| | |
|---|---|
| Injection system: | Common rail with solenoid type injectors Delphi Injection System |
| Emissions control: | Conforms to Euro V limit values when combined with exhaust gas post-treatment system. |

The test fuel (RF06) is dosed with 0.5 mg/kg Na in the form of Sodium Naphthenate+10 mg/kg Dodecyl Succinic Acid (DDSA).

The test procedure consists of main run cycles followed by soak periods, before cold starts are carried out.

The main running cycle consist of two speed and load set points, repeated for 6 hrs, as seen below and in FIG. 1.

| Step | Speed (rpm) | Torque (N · m) | Duration (s) |
|---|---|---|---|
| 1 | 3750 | 280 | 1470 |
| 1-Ramp → 2 | — | — | 30 |
| 2 | 1000 | 10 | 270 |
| 2-Ramp → 1 | — | — | 30 |

The ramp times of 30 seconds are included in the duration of each step.

During the main run, parameters including, Throttle pedal position, ECU fault codes, Injector balance coefficient and Engine stalls are observed and recorded.

The engine is then left to soak at ambient temperature for 8 hrs.

After the soak period the engine is re-started. The starter is operated for 5 seconds; if the engine fails to start the engine is left for 60 seconds before a further attempt. A maximum of 5 attempts are allowed.

If the engine starts the engine is allowed to idle for 5 minutes. Individual exhaust temperatures are monitored and the maximum Temperature Delta is recorded. An increased variation in Cylinder-to-Cylinder exhaust temperatures is a good indication that injectors are suffering from IDID. Causing them to either open slowly or stay open to long.

Figure 2:
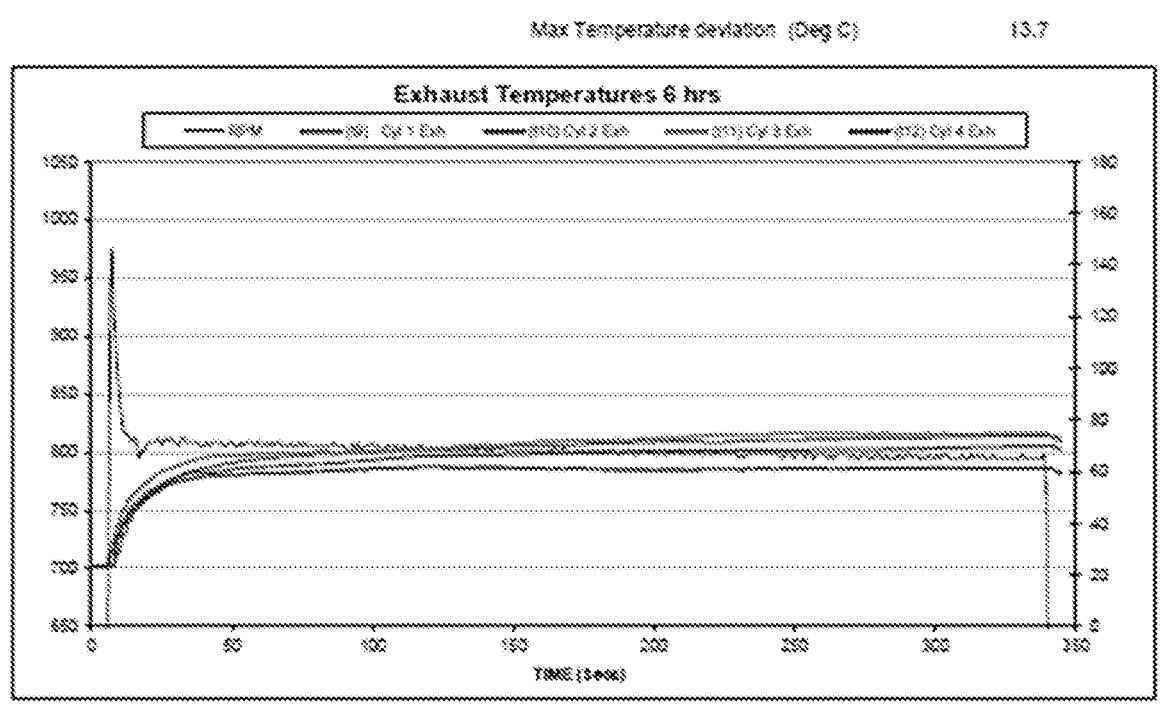
FIG. 2 is a graph of all exhaust temperatures with <30° C. deviation.

An example in FIG. 2 of all exhaust temperatures with <30° C. deviation, indicating no sticking caused by IDID.

The complete test comprises of 6× Cold Starts, although the Zero hour Cold Start does not form part of the Merit Rating and 5×6 hr Main run cycles, giving a total of 30 hrs engine running time.

The recorded data is inputted into the Merit Rating Chart. This allows a Rating to be produced for the test. Maximum rating of 10 shows no issues with the running or operability of the engine for the duration of the test.

An example below:

| | | Cold start | | | | | | | |
|---|---|---|---|---|---|---|---|---|---|
| | | Starting | | | | Exhaust temperature consistency | | | |
| | | | | | | | Exhaust | | |
| Cold Start | Start Y/N | Maximum Merits | Number of Attempts (1 = first start) | Deduction | Merits | Maximum Merits | Temperature Max Cyl. Deviation (° C.) | Deduction | Merits |
| #0 | | | | not rated | | | | | |
| #1 | Y | 5 | 1 | 0 | 5 | 5 | 21.8 | 0 | 5 |
| #2 | Y | 5 | 1 | 0 | 5 | 5 | 18.1 | 0 | 5 |
| #3 | Y | 5 | 1 | 0 | 5 | 5 | 15.5 | 0 | 5 |
| #4 | Y | 5 | 1 | 0 | 5 | 5 | 20.2 | 0 | 5 |
| #5 | Y | 5 | 1 | 0 | 5 | 5 | 22.6 | 0 | 5 |
| Total merits | | | | | 25 | | | | 25 |

| | | | Main run Operability | | | | | | |
|---|---|---|---|---|---|---|---|---|---|
| Main run | Maximum Merits | Number of ECU Fault resets | Deduction | Stall (Y/N) | Deduction | Max Pedal Position at 1000 rpm/10 N.m (%) | Deduction | Max Inject. Balancing Coeff. (rpm) | Deduction | Merits |
| #1 | 5 | 0 | 0 | N | 0 | 15.4 | 0 | 15 | 0 | 5 |
| #2 | 5 | 0 | 0 | N | 0 | 13.5 | 0 | 15 | 0 | 5 |
| #3 | 5 | 0 | 0 | N | 0 | 13.6 | 0 | 16 | 0 | 5 |
| #4 | 5 | 0 | 0 | N | 0 | 13.8 | 0 | 15 | 0 | 5 |
| #5 | 5 | 0 | 0 | N | 0 | 14.5 | 0 | 15 | 0 | 5 |
| | | | | | | | | | | 25 |
| Global Rating—Summary (Merit/10) | | | | | | | | | | 10 |

Example 5

The effectiveness of the additives of the invention in older traditional diesel engine types was assessed using a standard industry test—CEC test method No. CEC F-23-A-01.

This test measures injector nozzle coking using a Peugeot XUD9 A/L Engine and provides a means of discriminating between fuels of different injector nozzle coking propensity. Nozzle coking is the result of carbon deposits forming between the injector needle and the needle seat. Deposition of the carbon deposit is due to exposure of the injector needle and seat to combustion gases, potentially causing undesirable variations in engine performance.

The Peugeot XUD9 A/L engine is a 4 cylinder indirect injection Diesel engine of 1.9 litre swept volume, obtained from Peugeot Citroen Motors specifically for the CEC PF023 method.

The test engine is fitted with cleaned injectors utilising unflatted injector needles. The airflow at various needle lift positions have been measured on a flow rig prior to test. The engine is operated for a period of 10 hours under cyclic conditions.

| Stage | Time (secs) | Speed (rpm) | Torque (Nm) |
|---|---|---|---|
| 1 | 30 | 1200 ± 30 | 10 ± 2 |
| 2 | 60 | 3000 ± 30 | 50 ± 2 |
| 3 | 60 | 1300 ± 30 | 35 ± 2 |
| 4 | 120 | 1850 ± 30 | 50 ± 2 |

The propensity of the fuel to promote deposit formation on the fuel injectors is determined by measuring the injector nozzle airflow again at the end of test, and comparing these values to those before test. The results are expressed in terms of percentage airflow reduction at various needle lift positions for all nozzles. The average value of the airflow reduction at 0.1 mm needle lift of all four nozzles is deemed the level of injector coking for a given fuel.

The results of this test using the specified additive combinations of the invention are shown in table 3. In each case the specified amount of active additive was added to an RF06 base fuel meeting the specification given in table 2 (example 5) above.

The invention claimed is:

1. A composition comprising a diesel fuel and a quaternary ammonium compound of formula (I):

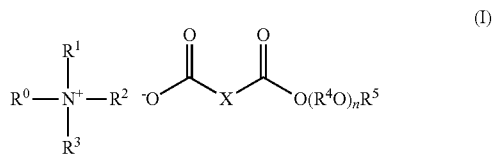

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen, X is $CH_2CHR$ or $CHRCH_2$ wherein R is an alkyl or alkenyl group having 20 to 24 carbon atoms.

2. A method of improving the performance of an engine, the method comprising combusting in the engine a diesel fuel composition comprising as an additive a quaternary ammonium compound of formula (I):

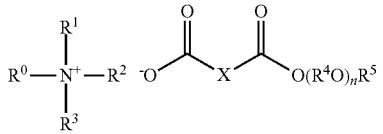

(I)

wherein $R^0$, $R^1$, $R^2$ and $R^3$ is each independently an optionally substituted hydrocarbyl group, X is a linking group, $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen; wherein X is $CH_2CHR$ or $CHRCH_2$ wherein R is an alkyl or alkenyl group having 20 to 24 carbon atoms.

3. The composition according to claim 1 wherein HOOCXCOO—$(R^4O)_n$—$R^5$ is derived from a hydrocarbyl substituted succinic acid or a hydrocarbyl substituted succinic anhydride.

4. The composition according to claim 1 wherein each $R^4$ is ethylene or propylene.

5. The composition according to claim 1 wherein $R^5$ is hydrogen and n is at least 1.

6. The composition according to claim 1 wherein $R^5$ is an optionally substituted alkyl group having 4 to 40 carbon atoms and n is from 0 to 40.

7. The composition according to claim 1 wherein each of $R^1$ and $R^2$ is independently an optionally substituted alkyl group having from 1 to 12 carbon atoms.

8. The composition according to claim 1 wherein $R^3$ is an alkyl or hydroxyalkyl group having 1 to 10 carbon atoms.

9. The composition according to claim 1 wherein $R^3$ is selected from the group consisting of:

(1) a polyisobutenyl group having a molecular weight of from 100 to 5000;

(2) an optionally substituted alkylene phenol moiety of formula (A) or (B)

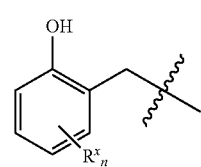

(A)

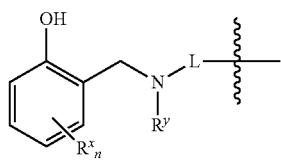

(B)

wherein n in structure (A) or (B) is 0 to 4, IV is an optionally substituted hydrocarbyl group, $R^y$ is an optionally substituted alkyl, alkenyl or aryl group; and L is a linking group; and (3) a succinimide moiety of formula:

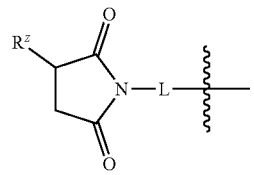

wherein $R^z$ is an optionally substituted hydrocarbyl group and L is a linking group.

10. The composition according to claim 1 wherein $R^0$ as is a group of formula:

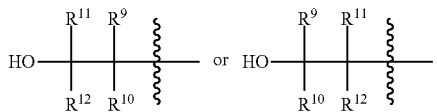

wherein each of $R^9$, $R^{10}$, $R^{11}$, $R^{12}$ is independently selected from hydrogen or an optionally substituted alkyl, alkenyl or aryl group.

11. The composition according to claim 1 wherein the quaternary ammonium compound is the reaction product of:

(a) a tertiary amine of formula $R^1R^2R^3N$ wherein each of, $R^1$, $R^2$ and $R^3$ is independently an optionally substituted alkyl group having 1 to 12 carbon atoms;

(b) an epoxide selected from styrene oxide, ethylene oxide, propylene oxide, butylene oxide, epoxyhexane, octene oxide, stilbene oxide, 2-ethylhexyl glycidyl ether, 1,2-epoxydodecane and other alkyl and alkenyl epoxides having 2 to 50 carbon atoms; and (c) a compound of formula HOOCXCOO—$(R^4O)_n$—$R^5$ wherein X is $CH_2CHR$ or $CHRCH_2$ wherein R is an alkyl or alkenyl group having 20 to 24 carbon atoms; and n is more than 1, $R^4$ is an ethylene or propylene group and $R^5$ is hydrogen; or n is 0 and $R^5$ is a C1 to C20 alkyl group.

12. The composition according to claim 1 wherein the quaternary ammonium compound is the reaction product of:

(a) a tertiary amine of formula $R^1R^2R^3N$ wherein each of, $R^1$, $R^2$ and $R^3$ is independently an alkyl or hydroxyalkyl group having 1 to 6 carbon atoms;

(b) an epoxide selected from propylene oxide, butylene oxide and 2-ethylhexyl glycidyl ether; and (c) a compound of formula HOOCXCOO—$(R^4O)_n$—$R^5$ which is the reaction product of a succinic acid or anhydride having a $C_{20}$ to $C_{24}$ alkyl or alkenyl substituent and an alcohol selected from polypropylene glycol having a number average molecular weight of 300 to 800, 2-ethylhexanol and butanol.

13. The composition according to claim 1 further comprising one or more detergents selected from the group consisting of:

(i) a further quaternary ammonium salt additive;

(ii) the product of a Mannich reaction between an aldehyde, an amine and an optionally substituted phenol;

(iii) the reaction product of a carboxylic acid-derived acylating agent and an amine;

(iv) the reaction product of a carboxylic acid-derived acylating agent and hydrazine;

(v) a salt formed by the reaction of a carboxylic acid with di-n-butylamine or tri-n-butylamine;

(vi) the reaction product of a hydrocarbyl-substituted dicarboxylic acid or anhydride and an amine compound or salt which product comprises at least one amino triazole group; and (vii) a substituted polyaromatic detergent additive.

14. The composition according to claim 1 wherein the composition comprises a mixture of two or more quarternary ammonium salt additives.

15. The method as defined in claim 2 wherein the additive is used as a detergent to combat deposits in a diesel fuel composition in a diesel engine.

16. The method according to claim 2 which is carried out in a diesel engine having a pressure in excess of 1350 bar.

17. The method according to claim 2 which achieves "keep clean" performance.

18. The method according to claim 2 which achieves "clean up" performance.

19. The method according to claim 15 wherein the deposits are injector deposits.

20. The method according to claim 19 wherein the deposits are internal diesel injector deposits.

21. The method according to claim 2 which achieves an improvement in performance of one or more of:
a reduction in power loss of the engine;
a reduction in external diesel injector deposits;
a reduction in internal diesel injector deposits;
an improvement in fuel economy;
a reduction in fuel filter deposits;
a reduction in emissions; or
an increase in maintenance intervals.

22. The method according to claim 21 which provides an improvement in performance in diesel engines having a pressure in excess of 1350 bar and provides an improvement in performance in traditional diesel engines.

23. The composition according to claim 1 which further comprises one or more further additives selected from the group consisting of: lubricity improvers, corrosion inhibitors and cold flow improvers.

24. A method of preparing a fuel composition, the method comprising preparing a quaternary ammonium salt by reacting (a) a tertiary amine of formula $R^1R^2R^3N$ with (b) an acid-activated alkylating agent in the presence of (c) a compound of formula $HOOCXCOO\text{---}(R^4O)_n\text{---}R^5$, and adding the quaternary ammonium salt into the fuel;

wherein $R^4$ is an optionally substituted alkylene group, $R^5$ is hydrogen or an optionally substituted alkyl, alkenyl or aryl group, and n is 0 or a positive integer, provided that n is not 0 when $R^5$ is hydrogen; and wherein n is a positive integer and/or X is $CH_2CHR$ or $CHRCH_2$ wherein R is an alkyl or alkenyl group having 20 to 24 carbon atoms.

* * * * *